United States Patent [19]

Vedvick et al.

[11] Patent Number: 5,258,302
[45] Date of Patent: Nov. 2, 1993

[54] DNA FOR EXPRESSION OF APROTININ IN METHYLOTROPHIC YEAST CELLS

[75] Inventors: Thomas S. Vedvick, Carlsbad; Michael E. Engel, La Jolla; Mary S. Urcan, San Diego; Richard G. Buckholz, Encinitas; Jennifer A. Kinney, San Diego, all of Calif.

[73] Assignee: The Salk Institute Biotechnology/Industrial Associates, Inc., San Diego, Calif.

[21] Appl. No.: 560,618

[22] Filed: Jul. 30, 1990

Related U.S. Application Data

[63] Continuation-in-part of Ser. No. 547,985, Jul. 3, 1990, abandoned.

[51] Int. Cl.$^5$ .......................... C07K 7/10; C12N 1/19; C12N 15/15; C12P 21/02
[52] U.S. Cl. .......................... 435/254.23; 435/320.1; 530/300; 536/23.5
[58] Field of Search ................ 435/69.1, 252.3, 320.1, 435/69.2, 69.8, 255; 935/28, 48, 69; 530/300; 536/23.5

[56] References Cited

U.S. PATENT DOCUMENTS

| | | | |
|---|---|---|---|
| 4,837,148 | 6/1989 | Cregg | 435/172.3 |
| 4,855,231 | 8/1989 | Stroman et al. | 435/69.1 |
| 4,882,279 | 11/1989 | Cregg | 435/172.3 |
| 4,929,555 | 5/1990 | Cregg et al. | 435/172.3 |

OTHER PUBLICATIONS

Norris et al. "Aprotinin and Aprotinin Analogues Expressed in Yeast" Biological Chemistry Hoppe-Seyler 371 (suppl):37-42 (Jun. 1989).

Kingsman et al. "Heterologous Gene Expression in *S. cerevisiae*" Biotechnology and Genetic Engineering Reviews 3:377-416 (Sep. 1985).

*Primary Examiner*—Richard A. Schwartz
*Assistant Examiner*—James Ketter
*Attorney, Agent, or Firm*—Fitch, Even, Tabin & Flannery

[57] ABSTRACT

Biologically active aprotinin (APR) molecules, naturally occurring, relatively short, single chain polypeptides, are prepared by growing methylotrophic yeast transformants containing in their genome at least one copy of a DNA sequence operably encoding APR, in operational association with a DNA sequence encoding the *S. cerevisiae* alpha mating factor pre-pro sequence (including a processing sequence selected from lys-arg-(glu-ala)$_x$, wherein x is an integer falling in the range of 0-3), both under the regulation of a promoter region of a gene of a methylotrophic yeast, under conditions allowing expression of said DNA sequences, and secretion of APR molecules into the culture medium.

Also disclosed are novel DNA fragments and novel recombinant yeast strains which are useful in the practice of the present invention.

9 Claims, 14 Drawing Sheets

```
                                                              60
1    GGATCCAGACCTGACTTCTGTCTAGAGCCACCATACACTGGACCATGCAAGGCCCGTATT
     ----------+---------+---------+---------+---------+---------+
     CCTAGGTCTGGACTGAAGACAGATCTCGGTGGTATGTGACCTGGTACGTTCCGGGCATAA
       ArgProAspPheCysLeuGluProProTyrThrGlyProCysLysAlaArgIle 120
61   ATTAGATACTTTTACAACGCTAAGGCCGGACTGTGTCAAACTTTCGTTTACGGTGGATGT
     ----------+---------+---------+---------+---------+---------+
     TAATCTATGAAAATGTTGCGATTCCGGCCTGACACAGTTTGAAAGCAAATGCCACCTACA
       IleArgTyrPheTyrAsnAlaLysAlaGlyLeuCysGlnThrPheValTyrGlyGlyCys 180
121  AGAGCTAAGAGAAACAACTTCAAGTCTGCTGAGGACTGTATGAGAACCTGTGGTGGTGCT
     ----------+---------+---------+---------+---------+---------+
     TCTCGATTCTCTTTGTTGAAGTTCAGACGACTCCTGACATACTCTTGGACACCACCACGA
       ArgAlaLysArgAsnAsnPheLysSerAlaGluAspCysMetArgThrCysGlyGlyAla

181  AAGCTT   186
     ------
     TTCGAA
```

*FIG. 1*

DNA FOR EXPRESSION OF APROTININ IN METHYLOTROPHIC YEAST CELLS

This application is a continuation-in-part of U.S. Ser. No. 547,985, filed Jul. 3, 1990, now abandoned.

FIELD OF THE INVENTION

This invention relates to a process of recombinant DNA technology for producing aprotinin (APR) peptides in methylotrophic yeast such as *Pichia pastoris*. The invention further relates to the methylotrophic yeast transformants, DNA fragments and expression vectors used for their production and cultures containing same.

BACKGROUND OF THE INVENTION

Aprotinin is a polypeptide of 58 amino acids with a molecular weight of 6512 daltons. This single chain protein has three disulfide bridges, linking cysteines at position (5-55), (14-38), and (30-51). These disulfide bonds, along with numerous hydrogen bonds and hydrophilic interactions, maintain the compact acid-stable tertiary structure of this molecule. Aprotinin has been well studied because of its small size, tremendous stability and function.

Aprotinin is a potent, naturally occurring enzyme inhibitor which inhibits proteolytic enzymes of the serine protease family. It is commonly isolated from a variety of bovine tissues including lung, parotid gland, spleen, liver, and pancreas. Specific enzymes known to be inhibited by aprotinin include trypsin, chymotrypsin, kallikrein, and plasmin. Aprotinin is also known as Bovine Pancreatic Trypsin Inhibitor (BPTI) and Trypsin Kallikrein Inhibitor (TKI).

Aprotinin is the active ingredient of a drug which has found wide use for the treatment of traumatic hemorrhagic shock, inhibition of plasmin, preservation of blood cell function in acid citrate dextrose (ACD)-stored blood as well as many other applications. In general, aprotinin is useful in reducing pathologically elevated proteolytic enzyme activity to normal levels.

Aprotinin is also useful in preventing proteolytic damage of recombinant products, such as proteins, polypeptides, enzymes, proenzymes, and preprotein, during purification and isolation procedures. The optimum amount of aprotinin for use in total inhibition of proteinases must be determined on a case-by-case basis; however, micromolar concentrations of aprotinin are usually sufficient.

Aprotinin is used extensively in radioimmunoassays to prevent proteolytic damage of the ligand. Some of the radioimmunoassays that use aprotinin as a proteolytic enzyme inhibitor are assays of adrenocorticotropin, calcitonin, beta endorphin, glucagon, and renin somatostatin.

Considering the many clinical and research applications of aprotinin, a ready supply of aprotinin, such as that which would result from fermentation of aprotinin-expressing recombinant organisms, will be of great value to the medical and biotechnology fields.

Since isolation from natural sources is technically difficult, expensive, and time consuming, recent efforts have centered on the development of efficient recombinant methods for the production of APR.

Of the hosts widely used for the production of heterologous proteins, probably *E. coli* and *Saccharomyces cerevisiae* (Baker's yeast) are the best understood. However, *E. coli* tends to produce disulfide-bonded proteins such as APR in their reduced forms which frequently are not stable in the presence of endogenous bacterial proteases, and which tend to aggregate into inactive complexes. Attempts to overcome this problem, e.g., by employing a suitable leader sequence in order to produce soluble APR which could be readily recovered from the cell broth, resulted in other inconveniences, especially during purification of the product, since the bulk of the desired protein was associated with the cell paste.

For example, Auerswald, Schroder and Kottich, in *Biol. Chem. Hoppe Seyler* (Germany, West) 368, 1413-1425 (1987) disclose the synthesis, cloning and expression of recombinant aprotinin in *E. coli* using a synthetic gene formed by the fusion of DNA fragments of the aprotinin coding sequence. Product was expressed as a fusion protein with beta-galactosidase. Cyanogen bromide cleavage of the fusion protein, followed by purification and renaturation is required to produce biologically active product.

Marks, et al., in *J. Biol. Chem.* 261, pp. 7115–118 (1986), report the successful expression of bovine pancreatic trypsin inhibitor (BPTI) in *E. coli*. These workers were able to overcome the difficulties in producing disulfide-bonded proteins in *E. coli*, describing the production of correctly folded BPTI that was conformationally indistinguishable from native BPTI.

Other publications dealing with the recombinant production of aprotinin include European Patent Application Nos. 238,993, 244,627, and 208,539.

Yeasts can offer clear advantages over bacteria in the production of heterologous proteins, which include their ability to secrete heterologous proteins into the culture medium. Secretion of proteins from cells is generally superior to production of proteins in the cytoplasm. Secreted products are obtained in a higher degree of initial purity; and further purification of the secreted products is made easier by the absence of cellular debris. In the case of sulfhydryl-rich proteins, there is another compelling reason for the development of eukaryotic hosts capable of secreting such proteins into the culture medium: their correct tertiary structure is produced and maintained via disulfide bonds. This is because the secretory pathway of the cell and the extracellular medium are oxidizing environments which can support disulfide bond formation [Smith, et al., *Science*, 229, 1219 (1985)]; whereas, in contrast, the cytoplasm is a reducing environment in which disulfide bonds cannot form. Upon cell breakage, too rapid formation of disulfide linkages can result in random disulfide bond formation. Consequently, production of sulfhydryl-rich proteins, such as APR, containing appropriately formed disulfide bonds, can be best achieved by transit through the secretory pathway.

Secretion of aprotinin having the desired intramolecular disulfide bonds from *E. coli* is suggested in Japanese document No. 63230089 (assigned to Takeda Chemical Ind KK). The cited document contains no details as to the level of secretion or the purity of APR obtained, nor is there any suggestion that APR could be expressed in any other host system besides *E. coli*.

PCT International Application No. PCT/DK88/00138, bearing International Publication No. WO 89/01968, describes the production of aprotinin and aprotinin homologues in *S. cerevisiae* under the control of the *S. cerevisiae* triosephosphate isomerase promoter. The aprotinin and aprotinin homologues are encoded by autonomously replicating plasmid-borne DNA. The reported yields of aprotinin and homologues thereof are quite low, ranging from 1–13 mg of aprotinin per liter of fermentation broth.

In view of the problems usually encountered with up-scaling the production of heterologous proteins in autonomous plasmid-based yeast systems, such as *S. cerevisiae*, and the low expression levels of aprotinin and aprotinin homologues achieved in reported work in *S. cerevisiae*, no motivation is provided by the art for one to further pursue the production of APR in *S. cerevisiae*. To overcome the major problems associated with the expression of recombinant gene products in *S. cerevisiae* (e.g., loss of selection for plasmid maintenance and problems concerning plasmid distribution, copy number and stability in fermentors operated at high cell density), a yeast expression system based on methylotrophic yeast, such as for example, *Pichia pastoris*, has been developed. A key feature of this unique system lies with the promoter employed to drive heterologous gene expression. This promoter, which is derived from a methanol-responsive gene of a methylotrophic yeast, is frequently highly expressed and tightly regulated (see, e.g., European Patent Application No. 85113737.2, published Jun. 4, 1986, under No. 0 183 071 and issued in the U.S. on Aug. 8, 1989, as U.S. Pat. No. 4,855,231). Another key feature of expression systems based on methylotrophic yeast is the ability of expression cassettes to stably integrate into the genome of the methylotrophic yeast host, thus significantly decreasing the chance of vector loss.

Although the methylotrophic yeast *P. pastoris* has been used successfully for the production of various [Cregg et al., *Bio/Technology* 5, 479 (1987)], lysozyme and invertase [Digan et al., *Developments in Industrial Microbiology* 29, 59 (1988); Tschopp et al., *Bio/Technology* 5, 1305 (1987)], endeavors to produce other heterologous gene products in *Pichia*, especially by secretion, have given mixed results. At the present level of understanding of methylotrophic yeast expression systems, it is unpredictable whether a given gene can be expressed to an appreciable level in such yeast or whether the yeast host will tolerate the presence of the recombinant gene product in its cells. In addition, it is unpredictable whether desired or undesired proteolysis of the primary product will occur, and if the resulting proteolytic products are biologically active. Further, it is especially difficult to foresee if a particular protein will be secreted by the methylotrophic yeast host, and if it is, at what efficiency. Even for the non-methylotrophic yeast *S. cerevisiae*, which has been considerably more extensively studied than *P. pastoris*, the mechanism of protein secretion is not well defined and understood.

SUMMARY OF THE INVENTION

In accordance with the present invention, we have developed an expression system suitable for the production of biologically active aprotinin (APR) molecules. The present invention provides a powerful method for the production of secreted APR peptides in methylotrophic yeast. In addition, the invention method can easily be scaled up from shake-flask cultures to large scale fermentors with no loss in APR productivity. Moreover, the invention method can readily be scaled up without the need for making major changes in the fermentation conditions used for the growth of the transformed strains relative to the conditions used for small scale growth of transformed strains.

We have surprisingly found that biologically active APR peptides can very efficiently be produced in, and secreted from, methylotrophic yeast, such as, for example, *P. pastoris*. This is accomplished by transforming a methylotrophic yeast with, and preferably integrating into the yeast genome, at least one copy of a first DNA sequence operably encoding an APR peptide, wherein said first DNA sequence is operably associated with a second DNA sequence encoding the *S. cerevisiae* alpha-mating factor (AMF) pre-pro sequence (including a processing sequence selected from lys-arg-(glu-ala)$_x$, wherein x is an integer falling in the range of 0–3), and wherein both of said DNA sequences are under the regulation of a methanol responsive promoter region of a gene of a methylotrophic yeast. Methylotrophic yeast cells containing in their genome at least one copy of these DNA sequences efficiently produce and secrete biologically active APR peptides into the medium.

The present invention is directed to the above aspects and all associated methods and means for accomplishing such. For example, the invention includes the technology requisite to suitable growth of the methylotrophic yeast host cells, fermentation, and isolation and purification of the APR gene product.

BRIEF DESCRIPTION OF THE DRAWINGS

FIG. 1 provides the nucleotide sequence of a synthetic aprotinin gene.

DETAILED DESCRIPTION OF THE INVENTION

Figure 2:
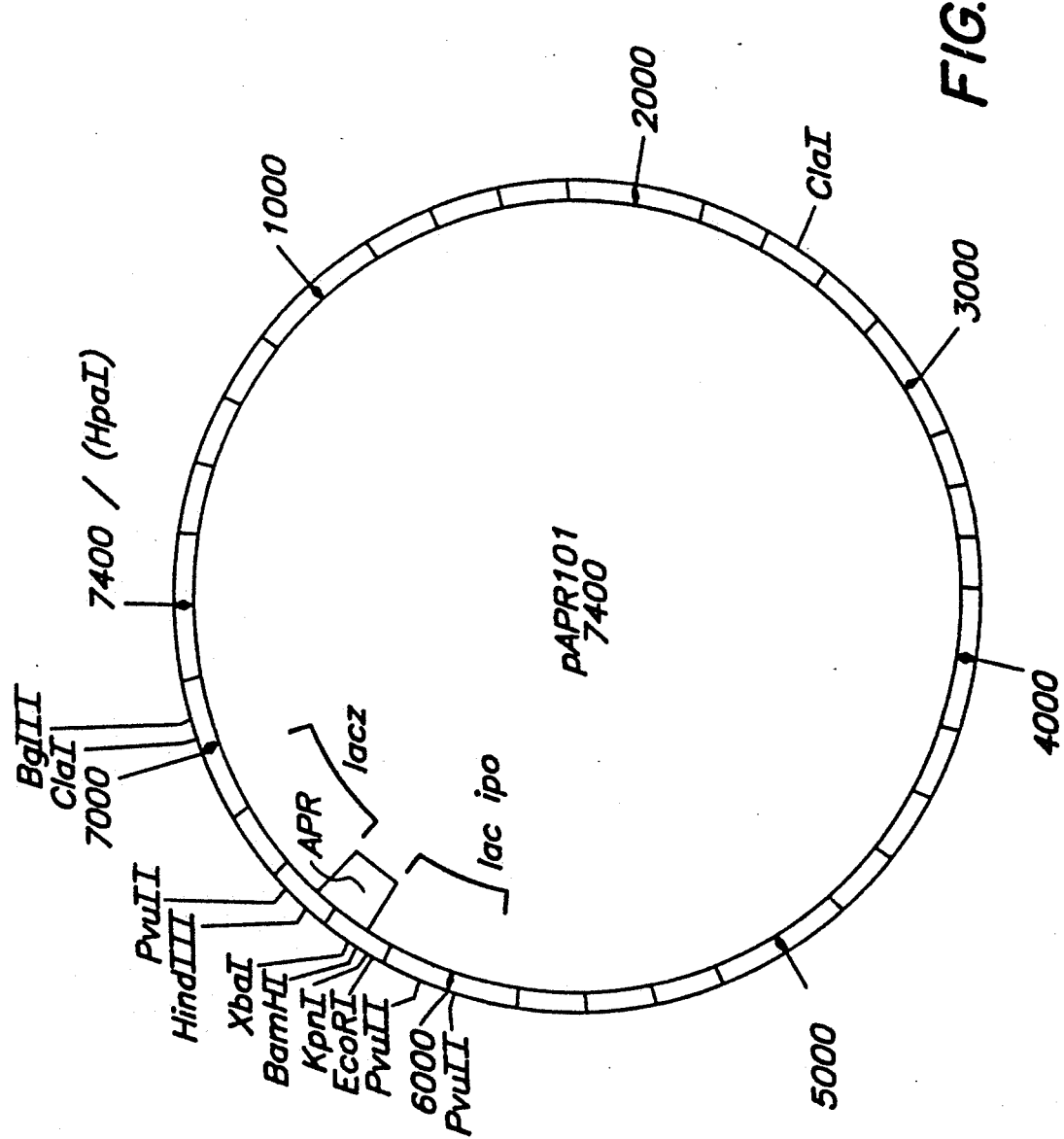
FIG. 2 is a restriction map of plasmid pAPR101.

In accordance with the present invention, there is provided a DNA fragment containing at least one copy of an expression cassette comprising in the reading frame direction of transcription, the following DNA sequences:
  (i) a promoter region of a methanol responsive gene of a methylotrophic yeast,
  (ii) a DNA sequence encoding a polypeptide consisting of:
    (a) the *S. cerevisiae* AMF pre-pro sequence, including a processing sequence selected from lys-arg-(glu-ala)$_x$, wherein x is an integer falling in the range of 0–3; and
    (b) a DNA sequence encoding an aprotinin (APR) peptide; and
  (iii) a transcription terminator functional in a methylotrophic yeast,
wherein said DNA sequences are operationally associated with one another for transcription of the sequences encoding said polypeptide.

The DNA fragment according to the invention can be transformed into methylotrophic yeast cells as a linear fragment flanked by DNA sequences having sufficient homology with a target gene to effect integration of said DNA fragment therein. In this case integration takes place by replacement at the site of the target gene. Alternatively, the DNA fragment can be part of a circular plasmid, which may be linearized to facilitate integration, and will integrate by addition at a site of homology between the host and the plasmid sequence.

In accordance with another embodiment of the present invention, there is provided an expression vector containing at least one copy of an expression cassette as described hereinabove.

According to another aspect of the present invention, there are provided novel methylotrophic yeast cells containing in their genome at least one copy of the above described DNA fragment.

According to a still further embodiment of the present invention, there is provided a process for producing APR peptides by growing methylotrophic yeast transformants containing in their genome at least one copy of a DNA sequence operably encoding an APR peptide, operably associated with DNA encoding the *S. cerevisiae* AMF pre-pro sequence (including a processing sequence selected from lys-arg-(glu-ala)$_x$, wherein x is an integer falling in the range of 0–3), both under the regulation of a promoter region of a methanol responsive gene of a methylotrophic yeast, under conditions allowing the expression of said DNA sequence in said transformants and secreting APR peptides into the culture medium. Cultures of viable methylotrophic yeast cells capable of producing APR peptides are also within the scope of the present invention.

The polypeptide product produced in accordance with the present invention is secreted to the culture medium at surprisingly high concentrations; the level of APR peptides secretion is about two orders of magnitude (i.e., about 100 times) higher than the *S. cerevisiae* results published in the literature (see WO 20 89/01968). In addition to the unique properties of the invention expression system, the excellent results obtained in the practice of the present invention are also due to the fact that the *S. cerevisiae* alpha-mating factor pre-pro sequence functions unexpectedly well to direct secretion of APR peptides in methylotrophic yeast.

The term "aprotinin" or "APR peptide" or simply "APR", as used throughout the specification and in the claims, refers to a polypeptide product which exhibits similar, in-kind, biological activities to natural aprotinin, as measured in recognized bioassays, and has substantially the same amino acid sequence as native APR. It will be understood that polypeptides deficient in one or more amino acids in the amino acid sequence reported in the literature for naturally occurring APR, or polypeptides containing additional amino acids or polypeptides in which one or more amino acids in the amino acid sequence of natural APR are replaced by other amino acids are within the scope of the invention, provided that they exhibit the functional activity of APR, e.g., inhibition of proteolytic enzymes of the serine protease family. The invention is intended to embrace all the allelic variations of APR. Moreover, as noted above, derivatives obtained by simple modification of the amino acid sequence of the naturally occurring product, e.g, by way of site-directed mutagenesis or other standard procedures, are included within the scope of the present invention. Proteolytic processed forms of APR, produced by transformed cells, and which exhibit similar biological activities to mature, naturally occurring APR, are also encompassed by the present invention.

The amino acids which occur in the various amino acid sequences referred to in the specification have their usual, three- and one-letter abbreviations, routinely used in the art, i.e.:

| Amino Acid | Abbreviation | |
|---|---|---|
| L-Alanine | Ala | A |
| L-Arginine | Arg | R |
| L-Asparagine | Asn | N |
| L-Aspartic acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

According to the present invention, APR peptides are produced by methylotrophic yeast cells containing in their genome at least one copy of a DNA sequence operably encoding APR peptides operably associated with DNA encoding the *S. cerevisiae* α-mating factor (AMF) pre-pro sequence (including a processing sequence selected from lys-arg-(glu-ala)$_x$, wherein x is an integer falling in the range of 0–3) under the regulation of a promoter region of a methanol responsive gene of a methylotrophic yeast.

The term "a DNA sequence operably encoding APR peptides" as used herein includes DNA sequences encoding APR or any other "APR peptide" as defined hereinabove. DNA sequences encoding APR are known in the art. They may be obtained by chemical synthesis or by transcription of messenger RNA (mRNA) corresponding to APR into complementary DNA (cDNA) and converting the latter into a double stranded cDNA. Chemical synthesis of a gene for human APR is, for example, disclosed by Auerswald, Schroder and Kottick, Suora. The requisite DNA sequence can also be removed, for example, by restriction enzyme digest of known vectors harboring the APR gene. Examples of such vectors and the means for their preparation can be taken from the following publications: Auerswald, Schroder and Kottick, Supra: Marks et al., Supra; and the like. The structure of a presently preferred APR gene used in accordance with the present invention is illustrated in FIG. 1 and is further elucidated in the examples.

Yeast species contemplated for use in the practice of the present invention are methylotrophs, i.e., species which are able to grow on methanol (as well as other)-carbon source nutriment. Species which have the biochemical pathways necessary for methanol utilization fall into four genera, i.e., *Candida, Hansenula, Pichia,* and *Torulopsis*. Of these, a substantial amount is known about the molecular biology of members of the species *Hansenula polymorpha* and *Pichia pastoris*.

The presently preferred yeast species for use in the practice of the present invention is *Pichia pastoris*, a known industrial yeast strain that is capable of efficiently utilizing methanol as the sole carbon and energy source.

There are a number of methanol responsive genes in methylotrophic yeast, the expression of each being controlled by methanol responsive regulatory regions (also referred to as promoters). Any of such methanol responsive promoters are suitable for use in the practice of the present invention. Examples of specific regulatory regions include the promoter for the primary alcohol oxidase gene from *Pichia pastoris* AOX1, the promoter for the secondary alcohol oxidase gene from *P. pastoris* AOX2, the promoter for the dihydroxyacetone synthase gene from *P. pastoris* (DAS), the promoter for the P40 gene from *P. pastoris*, the promoter for the catalase gene from *P. pastoris*, and the like.

The presently preferred promoter region employed to drive APR gene expression is derived from a methanol-regulated alcohol oxidase gene of *P. pastoris*. *P. pastoris* is known to contain two functional alcohol oxidase genes: alcohol oxidase I (AOX1) and alcohol oxidase II (AOX2). genes. The coding portions of the two AOX genes are closely homologous at both the DNA and the predicted amino acid sequence levels and share common restriction sites. The proteins expressed from the two genes have similar enzymatic properties but the promoter of the AOX1 gene is more efficient and more highly expressed; therefore, its use is preferred for APR expression. The AOX1 gene, including its promoter, has been isolated and thoroughly characterized; see Ellis et al., *Mol. Cell. Biol.* 5, 1111 (1985) and U.S. Pat. No. 4,855,231.

The expression cassette used for transforming methylotrophic yeast cells contains, in addition to a methanol responsive promoter of a methylotrophic yeast gene and the APR encoding DNA sequence (APR gene), a DNA sequence encoding the in-reading frame *S. cerevisiae* AMF pre-pro sequence, including a DNA sequence encoding a processing sequence selected from lys-arg-(glu-ala)$_x$, wherein x is an integer falling in the range of 0-3, and a transcription terminator functional in a methylotrophic yeast.

Figure 3:
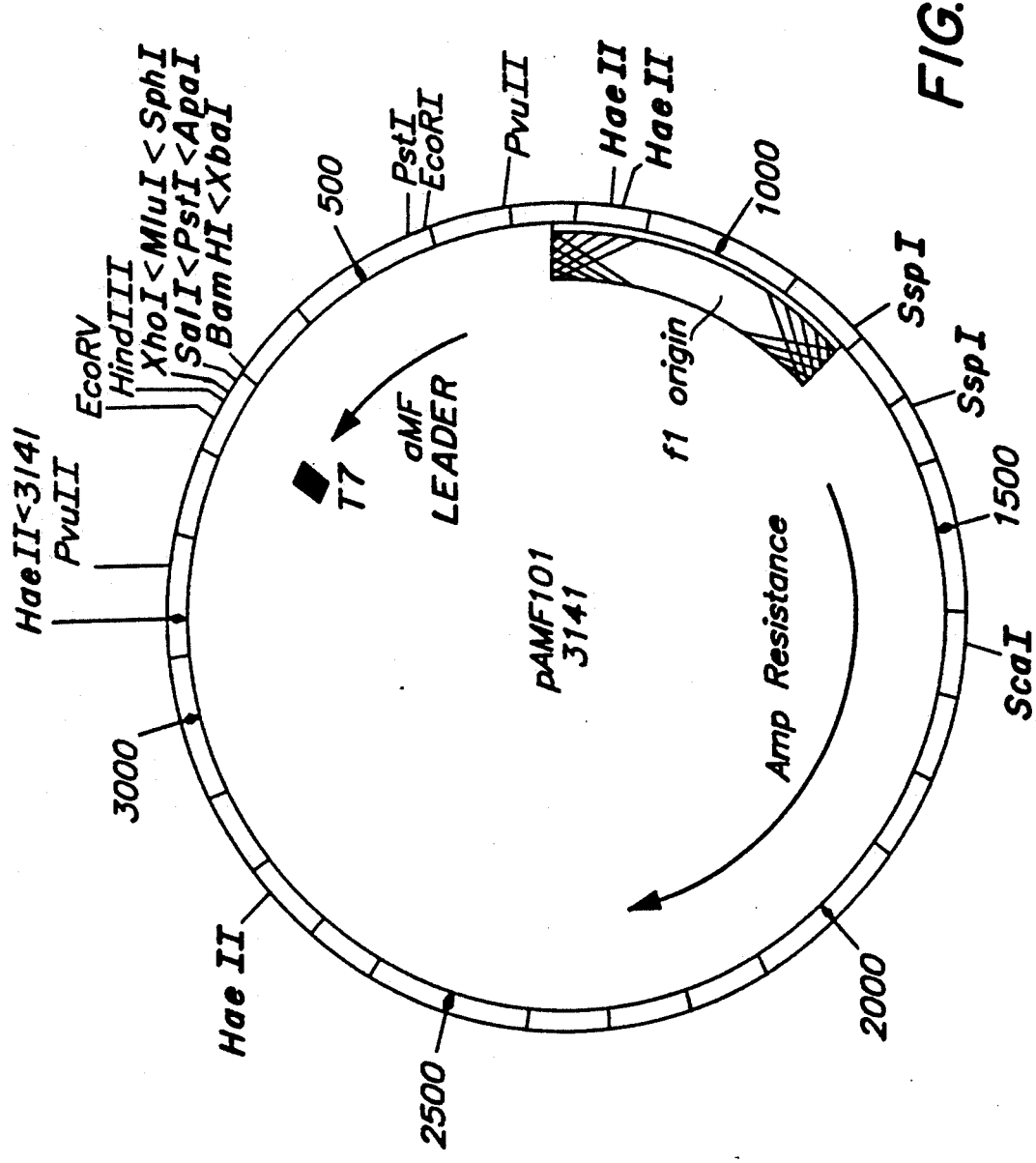
FIG. 3 is a restriction map of plasmid pAMF101.

The *S. cerevisiae* alpha-mating factor is a 13-residue peptide, secreted by cells of the "alpha" mating type, that acts on cells of the opposite "a" mating type to promote efficient conjugation between the two cell types and thereby formation of "a-alpha" diploid cells Thorner et al., *The Molecular Biology the Yeast Saccharomyces,* Cold Spring Harbor Laboratory, Cold Spring Harbor, N.Y., 143 (1981)]. The native AMF pre-pro sequence is a leader sequence contained in the AMF precursor molecule, and includes the lys-arg-glu-ala-glu-ala encoding sequence which is necessary for proteolytic processing and secretion (see e.g. Brake et al., *Proc. Natl. Acad. Sci.* U.S.A. 81: 4642 (1984)). The AMF pre-pro sequence employed in the practice of the present invention is a 267 bp fragment derived, in part, from plasmid pAMF101, which is shown in FIG. 3, and includes the processing sequence lys-arg-(glu-ala)$_x$.

The transcription terminator functional in a methylotrophic yeast used in accordance with the present invention has either (a) a subsegment which encodes a polyadenylation signal and polyadenylation site in the transcript, and/or (b) a subsegment which provides a transcription termination signal for transcription from the promoter used in the expression cassette. The term "expression cassette" as used herein, and throughout the specification and claims, refers to a DNA sequence which includes sequences functional for both the expression and the secretion processes. The entire transcription terminator is taken from a protein-encoding gene, which may be the same or different from the gene which is the source of the promoter.

For the practice of the present invention it is preferred that multiple copies of the above-described expression cassettes be contained on one DNA fragment, preferably in a head-to-tail orientation.

The DNA fragments according to the invention optionally further comprise a selectable marker gene. For this purpose, any selectable marker gene functional in methylotrophic yeast may be employed, i.e., any gene which confers a phenotype upon methylotrophic yeast cells, thereby allowing them to be identified and selectively grown from among a vast majority of untransformed cells. Suitable selectable marker genes include, for example, selectable marker systems composed of an auxotrophic mutant *P. pastoris* host strain and a wild type biosynthetic gene which complements the host's defect. For transformation of His4− *P. pastoris* strains, for example, the *S. cerevisiae* or *P. pastoris* HIS4 gene, or for transformation of Arg4− mutants, the *S. cerevisiae* ARG4 gene or the *P. pastoris* ARG4 gene, may be employed.

In addition, DNA fragments according to the invention optionally further comprise selectable marker genes which are functional in bacteria. Thus, any gene can be used which confers a phenotype on bacteria that allows transformed bacterial cells to be identified and selectively grown from among a vast majority of untransformed cells. This additional selectable marker enables DNA of the invention to be transformed into bacteria such as *E. coli* for amplification. Suitable selectable marker genes include the ampicillin resistance gene (Amp$^r$), and the like.

When it is contemplated to pass DNA of the invention through bacterial cells, it is desirable to include in the DNA construct a bacterial origin of replication, to ensure the maintenance of the invention DNA form generation to generation of the bacterial. Exemplary bacterial origins of replication include the f1-ori, and the like.

If the yeast host is transformed with a linear DNA fragment containing the APR gene under the regulation of a promoter region of a *P. pastoris* gene and AMF sequences necessary for processing and secretion, the expression cassette is integrated into the host genome by any of the gene replacement techniques known in the art, such as by one-step gene replacement [see e.g., Rothstein, *Methods Enzymol.* 101, 202 (1983); Cregg et al., *Bio/Technology* 5, 479 (1987); and U.S. Pat. No. 4,882,279] or by two-step gene replacement methods [see e.g., Scherer and Davis, *Proc. Natl. Acad. Sci.* U.S.A., 76, 4951 (1979)]. The linear DNA fragment is directed to the desired locus, i.e., to the target gene to be disrupted, by means of flanking DNA sequences having sufficient homology with the target gene to effect integration of the DNA fragment therein. One-step gene disruptions are usually successful if the DNA to be introduced has as little as 0.2 kb homology with the fragment locus of the target gene; it is however, preferable to maximize the degree of homology for efficiency.

If the DNA fragment according to the invention is contained within, or is an expression vector, e.g., a circular plasmid, one or more copies of the plasmid can be integrated at the same or different loci, by addition to the genome instead of by gene disruption. Linearization of the plasmid by means of a suitable restriction endonuclease facilitates integration.

The term "expression vector", as employed herein, is intended to include vectors capable of expressing DNA sequences contained therein, where such sequences are in operational association with other sequences capable of effecting their expression, i.e., promoter sequences. In general, expression vectors usually used in recombinant DNA technology are often in the form of "plasmids", i.e., circular, double-stranded DNA loops, which in their vector form are not bound to the chromosome. In the present specification the terms "vector" and "plasmid" are used interchangeably. However, the invention is intended to include other forms of expression vectors as well, which function equivalently.

In the DNA fragments of the present invention, the segments of the expression cassette(s) are said to be "operationally associated" with one another. The DNA sequence encoding APR peptides is positioned and oriented functionally with respect to the promoter, the DNA sequence encoding the S. cerevisiae AMF pre-pro sequence (including a processing sequence selected from lys-arg-(glu-ala)$_x$, wherein x is an integer falling in the range of 0–3), and the transcription terminator. Thus, the polypeptide encoding segment is transcribed under regulation of the promoter region, into a transcript capable of providing, upon translation, the desired polypeptide. Because of the presence of the AMF pre-pro sequence, the expressed APR product is found as a secreted entity in the culture medium. Appropriate reading frame positioning and orientation of the various segments of the expression cassette are within the knowledge of persons of ordinary skill in the art; further details are given in the Examples.

The DNA fragment provided by the present invention may include sequences allowing for its replication and selection in bacteria, especially E. coli. In this way, large quantities of the DNA fragment can be produced by replication in bacteria.

Methods of transforming methylotrophic yeast, such as, for example, Pichia pastoris, as well as methods applicable for culturing methylotrophic yeast cells containing in their genome a gene encoding a heterologous protein, are known generally in the art.

According to the invention, the expression cassettes are transformed into methylotrophic yeast cells either by the spheroplast technique, described by Cregg et al., Mol. Cell. Biol. 5, 3376 (1985) [see also U.S. Pat. No. 4,879,231] or by the whole-cell lithium chloride yeast transformation system [Ito et al., Agric. Biol. Chem. 48, 341 (1984)], with modification necessary for adaptation to methylotrophic yeast, such as P. pastoris [See European Patent Application No. 312,934]. The whole-cell lithium chloride method is frequently more convenient in that it does not require the generation and maintenance of spheroplasts. Thus, for the purpose of the present invention the whole cell method is preferred.

Positive transformants are characterized by Southern blot analysis [Maniatis et al., Molecular Cloning: A Laboratory Manual, Cold Spring Harbor Laboratory Press, Cold Spring Harbor, N.Y., U.S.A. (1982)] for the site of DNA integration; Northern blots Maniatis, Op. Cit., R. S. Zitomer and B. D. Hall, J. Biol. Chem, 251, 6320 (1976)]for methanol-responsive APR gene expression; and product analysis for the presence of secreted APR peptides in the growth media.

Transformed strains, which are of the desired phenotype and genotype, are grown in fermentors. For the large-scale production of recombinant DNA-based products in methylotrophic yeast, a three-stage, high cell-density, batch fermentation system is normally the preferred fermentation protocol employed. In the first, or growth stage, expression hosts are cultured in defined minimal medium with an excess of a non-inducing carbon source (e.g., glycerol). When grown on such carbon sources, heterologous gene expression is completely repressed, which allows the generation of cell mass in the absence of heterologous protein expression. Next, a short period of carbon source limitation growth is allowed. Subsequent to the period of growth under limiting conditions, methanol alone (referred to herein as "methanol excess fed-batch mode") or a limiting amount of a non-inducing carbon source plus methanol (referred to herein as "mixed-feed fed-batch mode") are added in the fermentor, inducing the expression of the APR gene driven by a methanol responsive promoter. This third stage is the so-called production stage.

The term "culture" means a propagation of cells in a medium conducive to their growth, and all subcultures thereof. The term "subculture" refers to a culture of cells grown from cells of another culture (source culture), or any subculture of the source culture, regardless of the number of subculturings which have been performed between the subculture of interest and the source culture.

According to a preferred embodiment of the present invention, the heterologous protein expression system used for APR production utilizes the promoter derived from the methanol-regulated AOX1 gene of P. pastoris, which is very efficiently expressed and tightly regulated. This gene can be the source of the transcription terminator as well. The presently preferred expression cassette comprises, operationally associated with one another, the P. pastoris AOX1 promoter, DNA encoding the S. cerevisiae AMF pre-pro sequence (including a processing sequence selected from lys-arg-(glu-ala)$_x$, wherein x is an integer falling in the range of 0–3), a DNA sequence encoding mature APR, and a transcription terminator derived from the P. pastoris AOX1 gene. Preferably, two or more of such expression cassettes are contained on one DNA fragment, in head-to-tail orientation, to yield multiple expression cassettes on a single contiguous DNA fragment. The presently preferred host cells to be transformed with multiple expression cassettes are P. pastoris cells having at least one mutation that can be complemented with a marker gene present on a transforming DNA fragment. Preferably His4− (GS115) or Arg4− (GS190) auxotrophic mutant P. pastoris strains are employed.

The fragment containing one or more expression cassette(s) is inserted into a plasmid containing a marker gene complementing the host's defect. pBR322-based plasmids, e.g., pA0815, are preferred. Insertion of one or more copies of the APR expression/secretion cassette into parent plasmid pA0815 produces plasmids pAPR105, pAPR205, and pAPR501.

To develop Mut− expression strains of P. pastoris (Mut refers to the methanol-utilization phenotype), the transforming DNA comprising the expression cassette(s) is (are) preferably integrated into the host genome by a one-step gene replacement technique. The expression vector is digested with an appropriate enzyme to yield a linear DNA fragment with ends homologous to the AOX1 locus by means of the flanking homologous sequences. This approach avoids the problems encountered with *S. cerevisiae,* wherein expression cassettes must be present on multicopy plasmids to achieve high level of expression. As a result of gene replacement, Mut⁻ strains are obtained. In Mut⁻ strains, the AOX1 gene is replaced with the expression cassette(s), thus decreasing the strains' ability to utilize methanol. A slow growth rate on methanol is maintained by expression of the AOX2 gene product. The transformants in which the expression cassette has integrated into the AOX1 locus by site-directed recombination can be identified by first screening for the presence of the complementing gene. This is preferably accomplished by growing the cells in media lacking the complementing gene product and identifying those cells which are able to grow by nature of expression of the complementing gene. Next, the selected cells are screened for their Mut phenotype by growing them in the presence of methanol and monitoring their growth rate.

To develop MUT+ APR-expressing strains, the fragment comprising one or more expression cassette(s) preferably is integrated into the host genome by transformation of the host with a linearized plasmid comprising the expression cassette(s). The integration is by addition at a locus or loci having homology with one or more sequences present on the transformation vector.

Positive transformants are characterized by Southern analysis for the site of DNA integration; by Northern analysis for methanol-responsive APR gene expression; and by product analysis for the presence of secreted APR peptides in the growth media. Methylotrophic yeast strains which have integrated one or multiple copies of the expression cassette at a desired site can be identified by Southern blot analysis. Strains which demonstrate enhanced levels of expression of APR may be identified by Northern or product analysis; however, this characteristic is not always easy to detect in shake-flask experiments.

Methylotrophic yeast transformants which are identified to have the desired genotype and phenotype are grown in fermentors. It is presently preferred to use the three-step production process described above. The level of APR secreted into the media can be determined by Western blot analysis of the media in parallel with an APR standard, using anti-APR antisera; by radioimmunoassay (RIA); by enzyme-inhibitor assay; or by HPLC after suitable pretreatment of the medium.

The invention will now be described in greater detail with reference to the following non-limiting examples.

EXAMPLES

*P. pastoris* is described herein as a model system for the use of methylotrophic yeast hosts. Other useful methylotrophic yeasts can be taken from four genera, namely *Candida, Hansenula, Pichia* and *Torulopsis.* Equivalent species from them may be used as hosts herein primarily based upon their demonstrated characterization of being supportable for growth and exploitation on methanol as a single carbon nutriment source. See, for example, Gleeson et al., *Yeast* 4, 1 (1988).

EXAMPLE 1

Construction of a Synthetic Gene Encoding Aprotinin; Plasmid pAPR101

The expression vector constructions disclosed in the present application were performed using standard procedures, as described, for example in Maniatis et al., Supra, and Davis et al., *Basic Methods in Molecular Biology,* Elsevier Science Publishing, Inc., New York (1986).

A synthetic aprotinin gene sequence (shown in FIG. 1) was formulated by back translation of the aprotinin amino acid sequence [see Kassell, B. et al. in *Biochem. Biophys. Res. Comm.* 18:255-258 (1965)] using a codon frequency computer program [University of Wisconsin Genetics Computer Group (UWGCG)] in combination with consensus data generated from known gene sequences of the yeast *Pichia pastoris.* Additionally, an XbaI site was included at nucleic acid position +18 to allow characterization of the gene during subcloning, and BamHI and HindIII sites were engineered into the 5' and 3' ends of the gene, respectively, to allow for subcloning the gene into pAMF101.

Eight synthetic oligonucleotides, consisting of two 30 mers and six 50 mers, were designed to construct an aprotinin gene containing these modifications. The eight synthetic nucleotides had the following sequences:

| | |
|---|---|
| #1: | 5'-GAT CCA GAC CTG ACT TCT GTC TAG AGC CAC-3' |
| #5: | 5'-AGC TTA GCA CCA CCA CAG GTT CTC ATA CAG-3' |
| #2: | 5'-CAT ACA CTG GAC CAT GCA AGG CCC GTA TTA TTA GAT ACT TTT ACA ACG CT-3' |
| #3: | 5'-AAG GCC GGA CTG TGT CAA ACT TTC GTT TAC GGT GGA TGT AGA GCT AAG AG-3' |
| #4: | 5'-AAA CAA CTT CAA GTC TGC TGA GGA CTG TAT GAG AAC CTG TGG TGG TGC TA-3' |
| #6: | 5'-TCC TCA GCA GAC TTG AAG TTG TTT CTC TTA GCT CTA CAT CCA CCG TAA AC-3' |
| #7: | 5'-GAA AGT TTG ACA CAG TCC GGC CTT AGC GTT GTA AAA GTA TCT AAT AAT AC-3' |
| #8: | 5'-GGG CCT TGC ATG GTC CAG TGT ATG GTG GCT CTA GAC AGA AGT CAG GTC TG-3' |

The synthetic aprotinin gene was prepared by ligation of these eight oligonucleotides. The number of overlapping base pairs was maximized to increase the specificity of ligation.

In preparation for annealing, the internal oligonucleotides without 5' overhangs (sequence nos. 2,3,4,6,7,and 8) were kinased with non-isotopic ATP [Maniatis, *Molecular Cloning, A Laboratory Manual,* Cold Springs Harbor Laboratory (Cold Springs Harbor, N.Y.; 982)]. The 5' end oligonucleotides were not kinased, to eliminate the potential for concatenation. A small amount of each internal oligonucleotide was kinased with γ-$^{32}$P-ATP (Maniatis, supra) to be used as a radioactive tag and to calculate the amount of recovered gene. One-hundred pmoles of each kinased oligonucleotide and 100 pmoles of each of the two unkinased 5' end oligonucleotides were annealed and ligated in a final volume of 200 μl. When a 175 μl sample of the ligation mixture was separated on a 2% agarose prep gel and stained with ethidium bromide, a sharp band representing the 176 bp synthetic aprotinin gene could be observed; this fragment was eluted with DE81 paper and ethanol precipitated. Using the percent of recovered radioactivity to calculate yield, it was determined that 0.51 μg, or 4.3 pmoles, of the purified aprotinin gene had been obtained.

The synthetic aprotinin gene was isolated from the gel and cloned into M13mp18, which had not been dephosphorylated since the external oligonucleotides comprising the BamHI and HindIII 5' overhangs were not kinased. Ligations of gene to vector were performed in 100:1 and 200:1 ratios at 14° C. for 36 hours. The ligation reactions were then digested with PstI to linearize any uncut vector and prevent its transformation into a bacterial host. The ligations were used to transform the E. coli strain JM103.

Duplicate plaque lifts were performed on each transformation plate and the filters were probed with the two terminal oligonucleotides (nos. 5 and 8) used in the construction of the aprotinin gene, which are complementary to the template strand. After hybridization and washing under stringent conditions (65° C., 15', 0.2 X SSC/0.2% SDS), 12 of the plaques that hybridized with both oligonucleotides were isolated from the screenings. These were grown for mini DNA preps and M13 template preps for sequencing.

Diagnostic restriction digests were performed on the mini DNA preps from each of the 12 plaques. The DNAs were digested with XbaI and HindIII, both unique restriction sites. Since XbaI cuts at nucleotide position no. 18 within the gene, and HindIII cuts at the 3' end of the gene, this double digest should yield a unique band of about 160 bp. Visualization of the digests on a 2% agarose gel, which had been stained with ethidium bromide, showed a band of about the correct size in most of the preparations.

M13 template preps of each of the 12 plaques were sequenced. One template was completely correct and was designated pAPR101 (see FIG. 2). Double-stranded pAPR101 was prepared and a portion was digested again with XbaI and HindIII to confirm the presence of the unique 160 bp band.

EXAMPLE 2

Construction of Aprotinin Expression Vectors a. pAPR105

Figure 4:
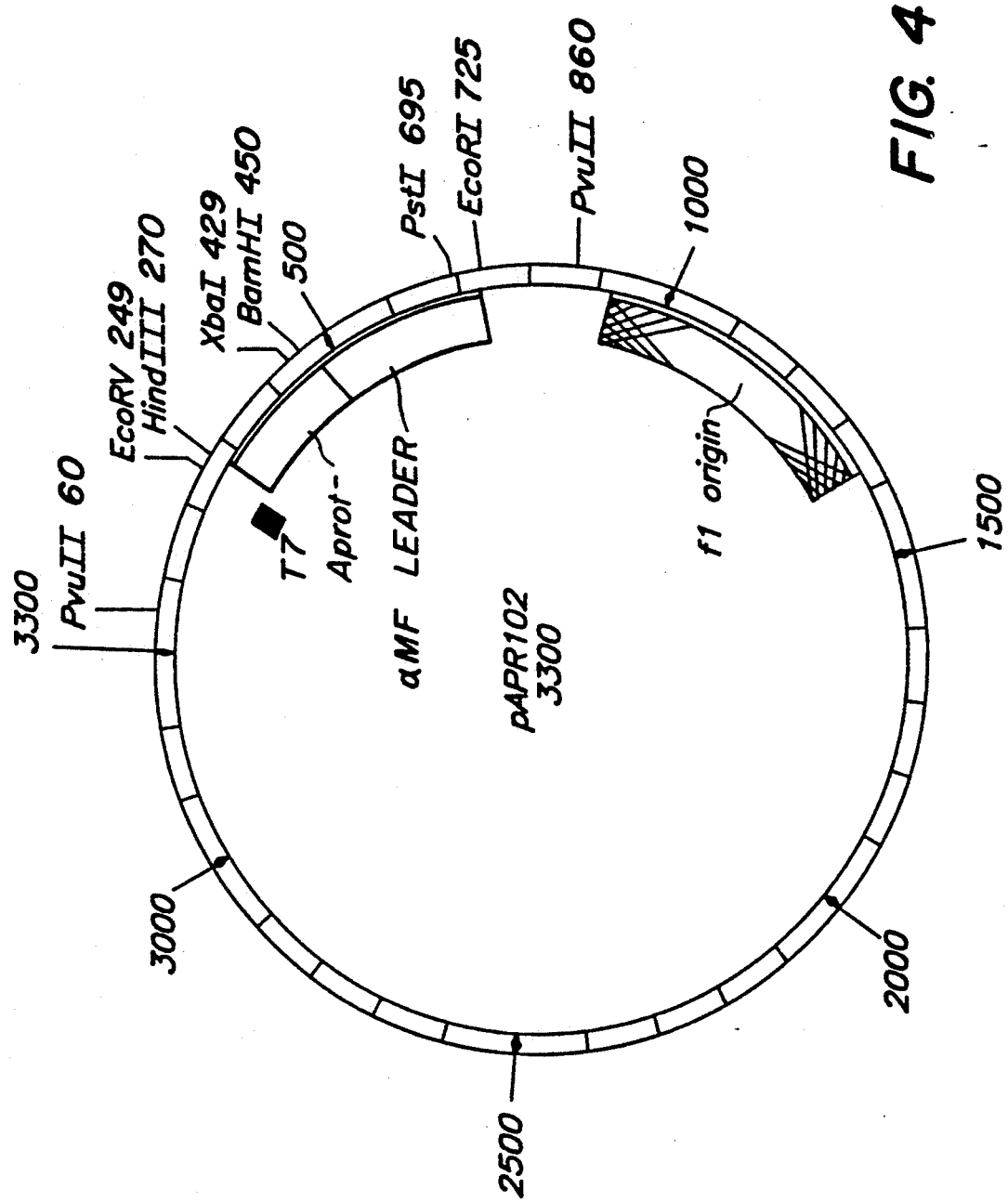
FIG. 4 is a restriction map of plasmid pAPR102.

Plasmid pAPR101 was digested with BamHI and HindIII and the 174 bp band representing the aprotinin gene was isolated from a 1.8% agarose gel. Plasmid pAMF101, a pIBI25-based plasmid that contains the S. cerevisiae α-mating factor (αMF) leader sequence, the f1 origin of replication (see FIG. 3; the construction of the plasmid is described in Example 6), and an ampicillin resistance marker was digested within its polylinker with BamHI and HindIII and dephosphorylated. 33 ng of the 174 bp pAPR101 fragment and 200 ng of the pAMF101 fragment (which provides a 3-fold molar excess of aprotinin-encoding fragment to the pAMF101 fragment) were ligated together and used to transform CJ236 cells. Amp ® colonies were selected and screened for correct plasmid, which yielded a diagnostic band of ~780 bp upon digestion with PvuII. Plasmid having the correct orientation was called pAPR102 (see FIG. 4).

Single stranded DNA from plasmid pAPR102 was mutagenized to fuse the αMF leader coding sequence directly to the aprotinin gene and delete the BamHI site. This was accomplished by site-directed in vitro mutagenesis using an oligonucleotide which has the following sequence:

540 -GGG TAT CTT TGG ATA AAA GAA GAC CTG ACT TCT GTC TAG A-3'

Figure 5:
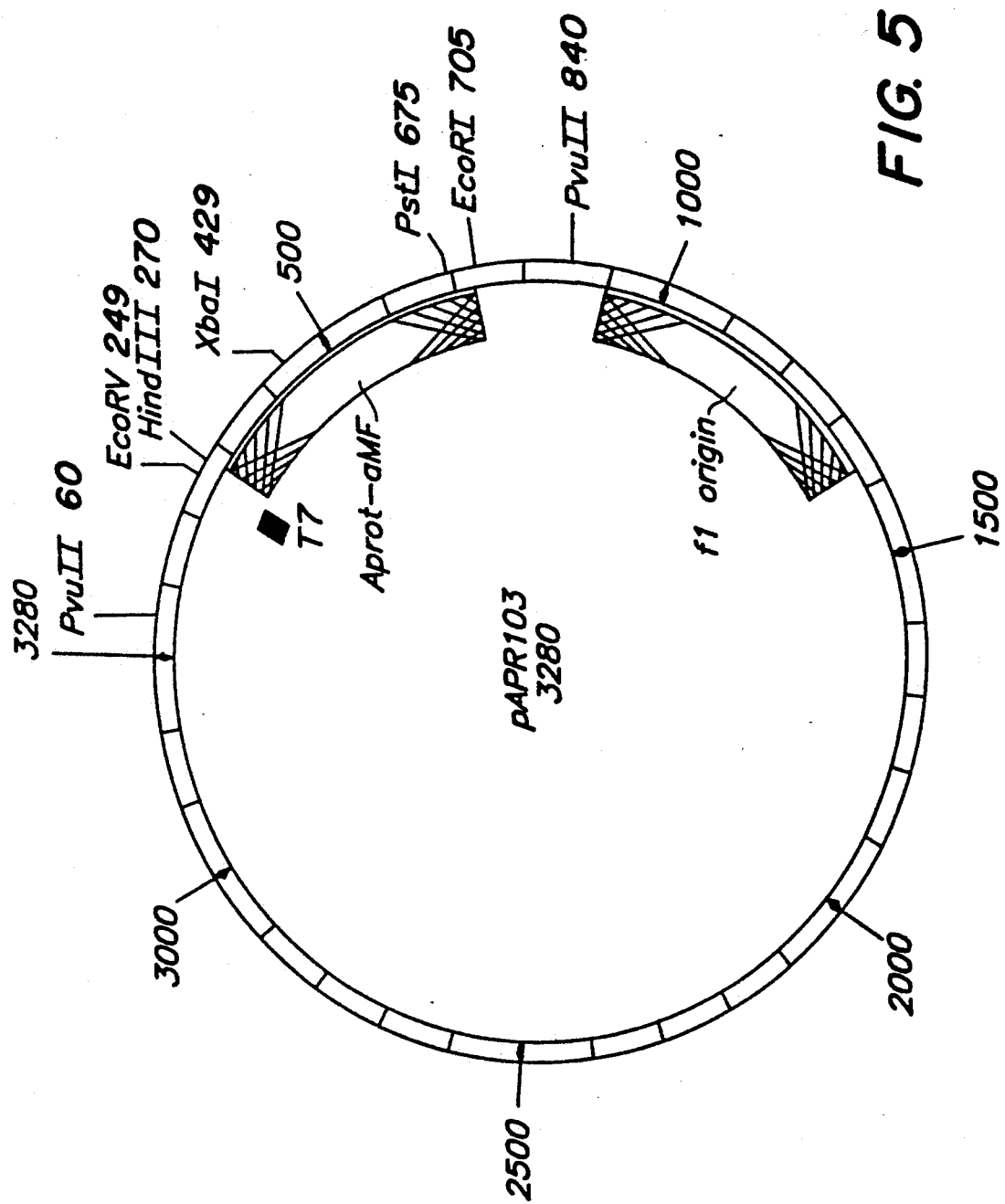
FIG. 5 is a restriction map of plasmid pAPR103.

The mutagenized DNA was used to transform MC1061 cells. Subsequent analysis of mini-prep DNA from transformants identified the plasmid having insert DNA in the correct orientation. Plasmid pAPR103 (see FIG. 5) was shown to be correct by a diagnostic digest with BamHI and PvuII, which yielded a band of 780 bp. Plasmid pAPR103 was transformed into CJ236 cells.

Single stranded DNA of plasmid pAPR103 was prepared and further mutagenized to insert a translation termination codon immediately after the aprotinin gene and to change the 3' HindIII site to an EcoRI site. Oligonucleotide APR102 was used for this mutagenesis, and had the following sequence:

5'ACC TGT GGT GGT GCT TAA GAA TTC TCC CTA TAG TGA GTC 3'

Figure 6:
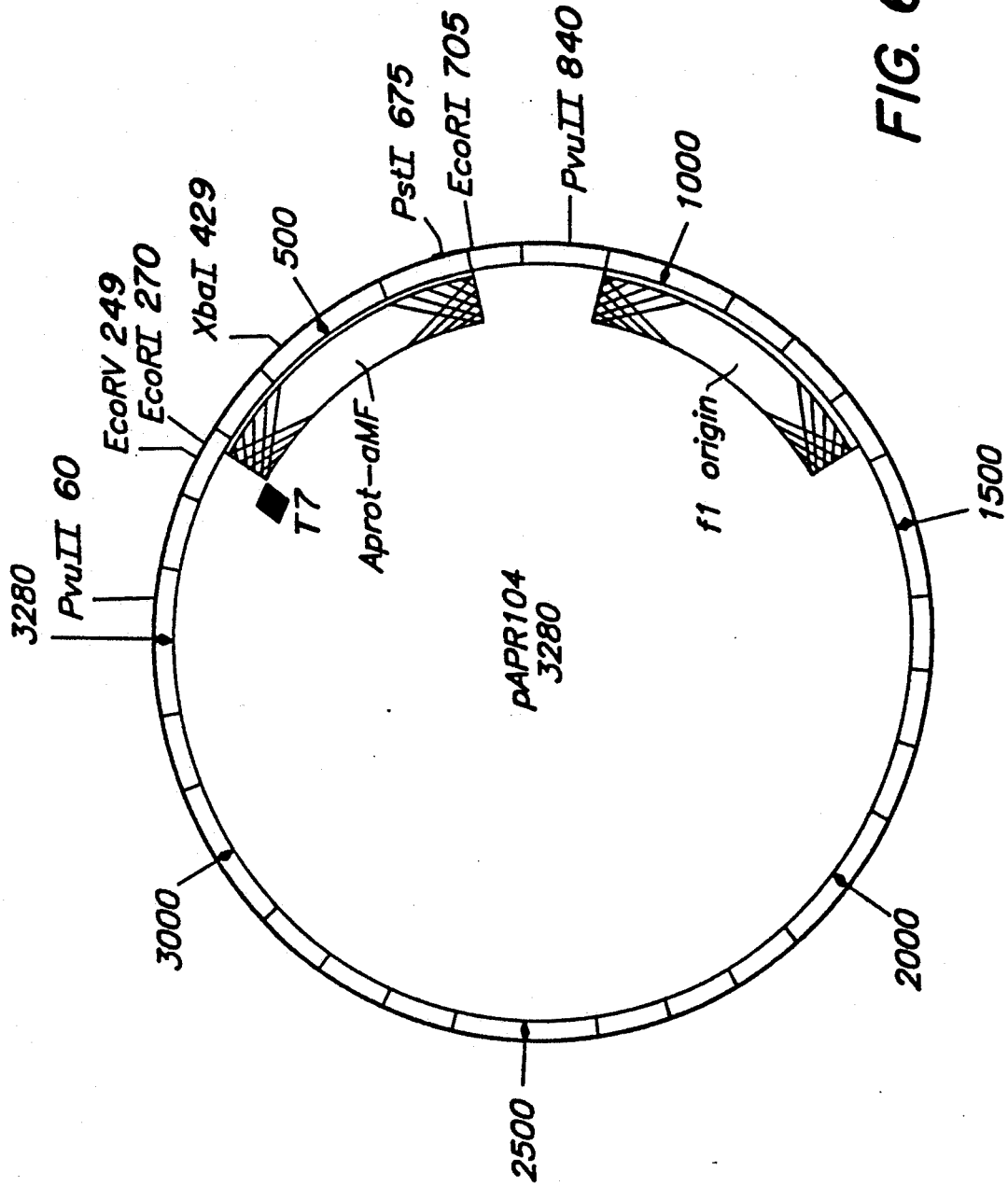
FIG. 6 is a restriction map of plasmid pAPR104.

Mutagenized DNA was transformed into MC1061 cells. Plasmid having the correct orientation of insert DNA was confirmed by diagnostic digest with EcoRI, which yielded a band of 434 bp. This plasmid is called pAPR104 (see FIG. 6).

Figure 7:
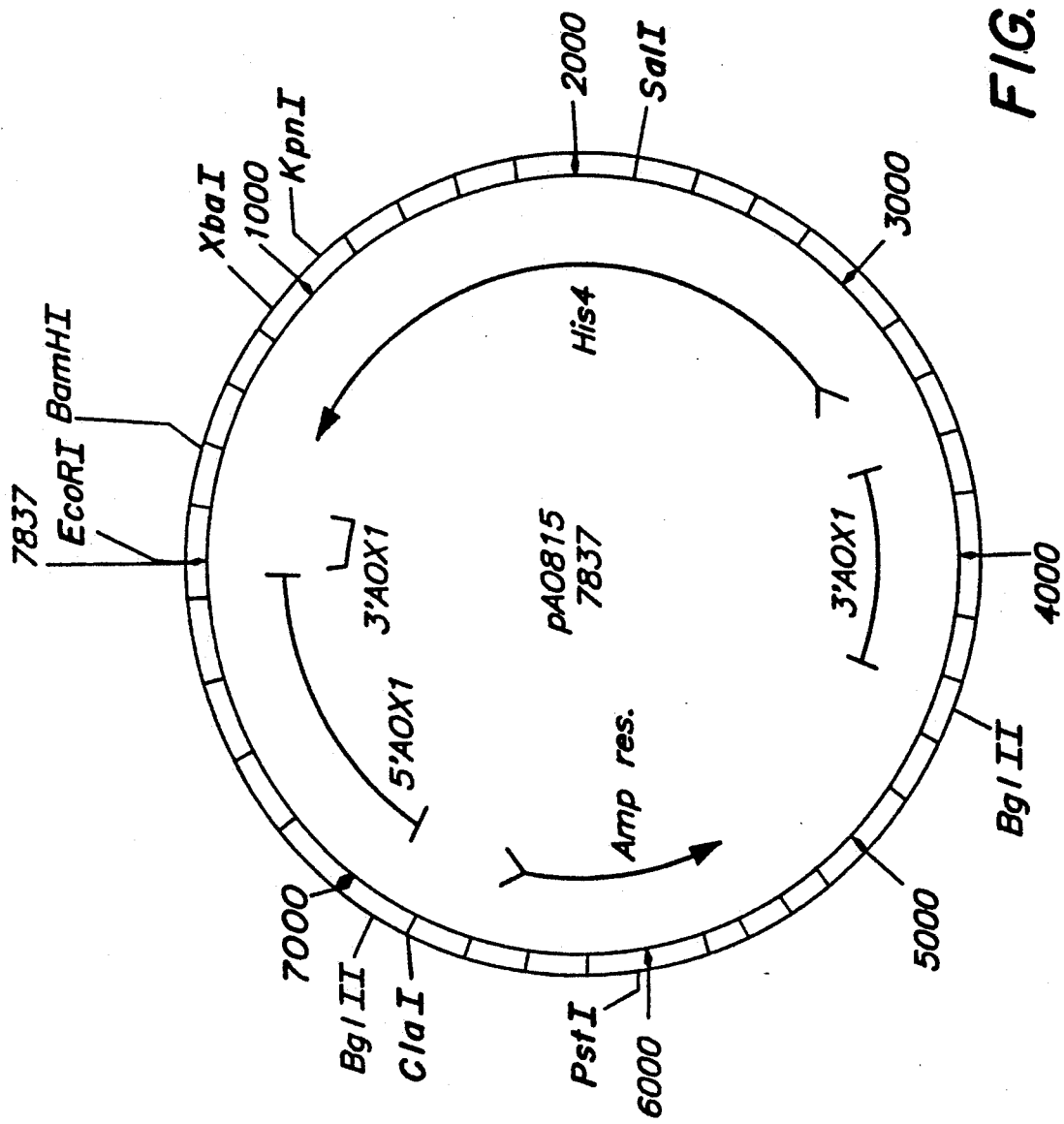
FIG. 7 is a restriction map of plasmid pAO815.
Figure 8A:
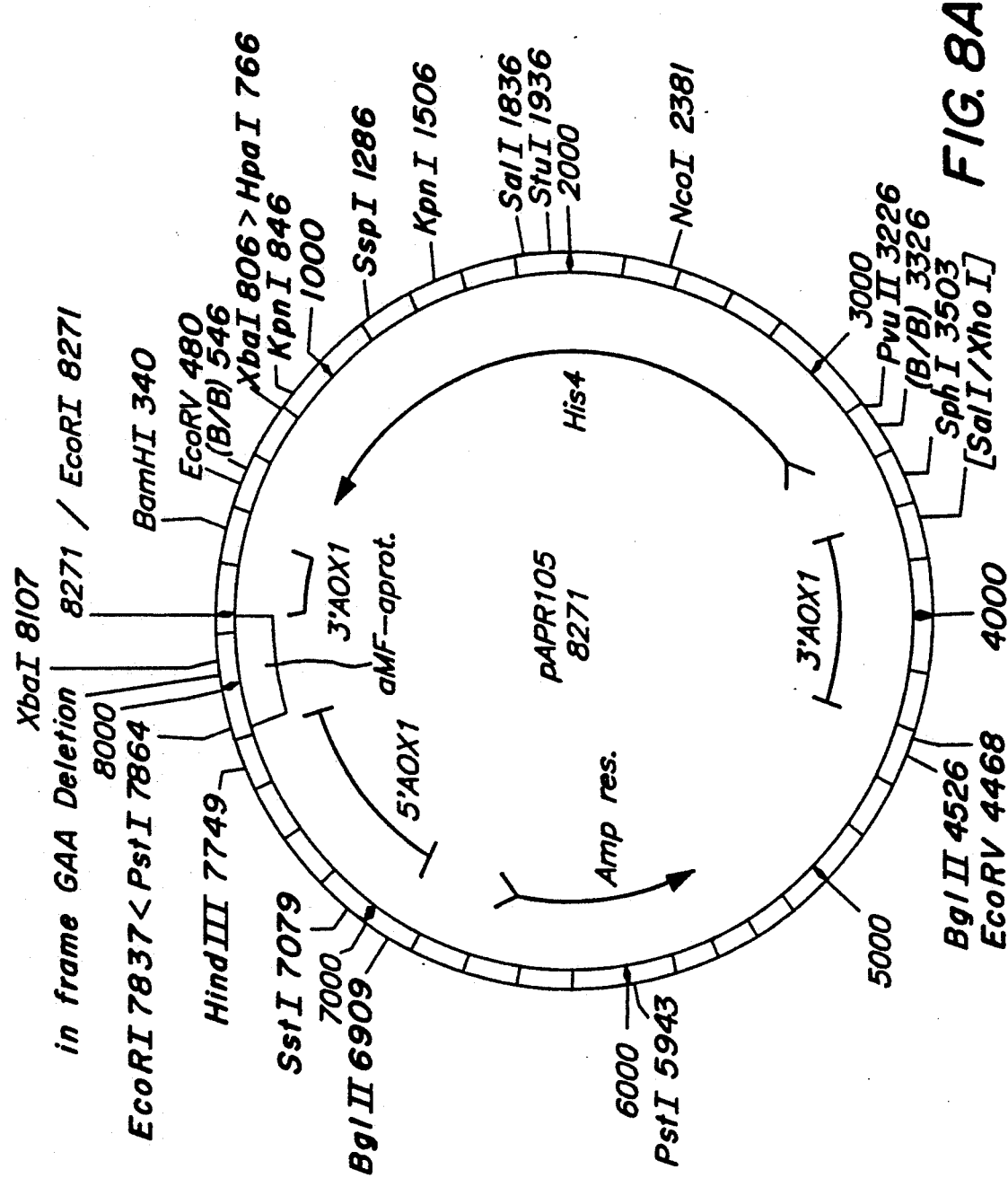
FIG. 8A is a restriction map of plasmid pAPR105 and FIG. 8B is a restriction map of plasmid pAPR205.

One expression plasmid which can be used to make aprotinin-expressing strains of P. pastoris was constructed by ligating 33 ng of the ~435 bp αMF-aprotinin EcoRI fragment of pAPR104 (isolated on a 1.5% agarose gel) with 200 ng of the ~7800 bp EcoRI-digested, phosphatase-treated fragment of vector pAO815 (see FIG. 7; which provides a 3-fold molar excess of αMF-aprotinin encoding fragment to the pAO815 fragment). A description of pAO815 and its preparation is provided in Example 7. The ligation reaction mixture was transformed into MC1061 cells and Amp ® colonies were selected. The aprotinin portion of the insert from one plasmid which showed the correct diagnostic pattern (called pAPR105; see FIG. 8A; the enclosure of restriction sites shown in the Figures in parenthesis designates sites that were available during the preparation of the plasmid, but were lost upon ligation) was sequenced and confirmed to be correct. Upon resequencing of pAPR105, an in-frame deletion of three nucleotides (GAA) was discovered at position 232 of the αMF pre-pro nucleotide sequence.

b. pAPR205

Figure 8B:
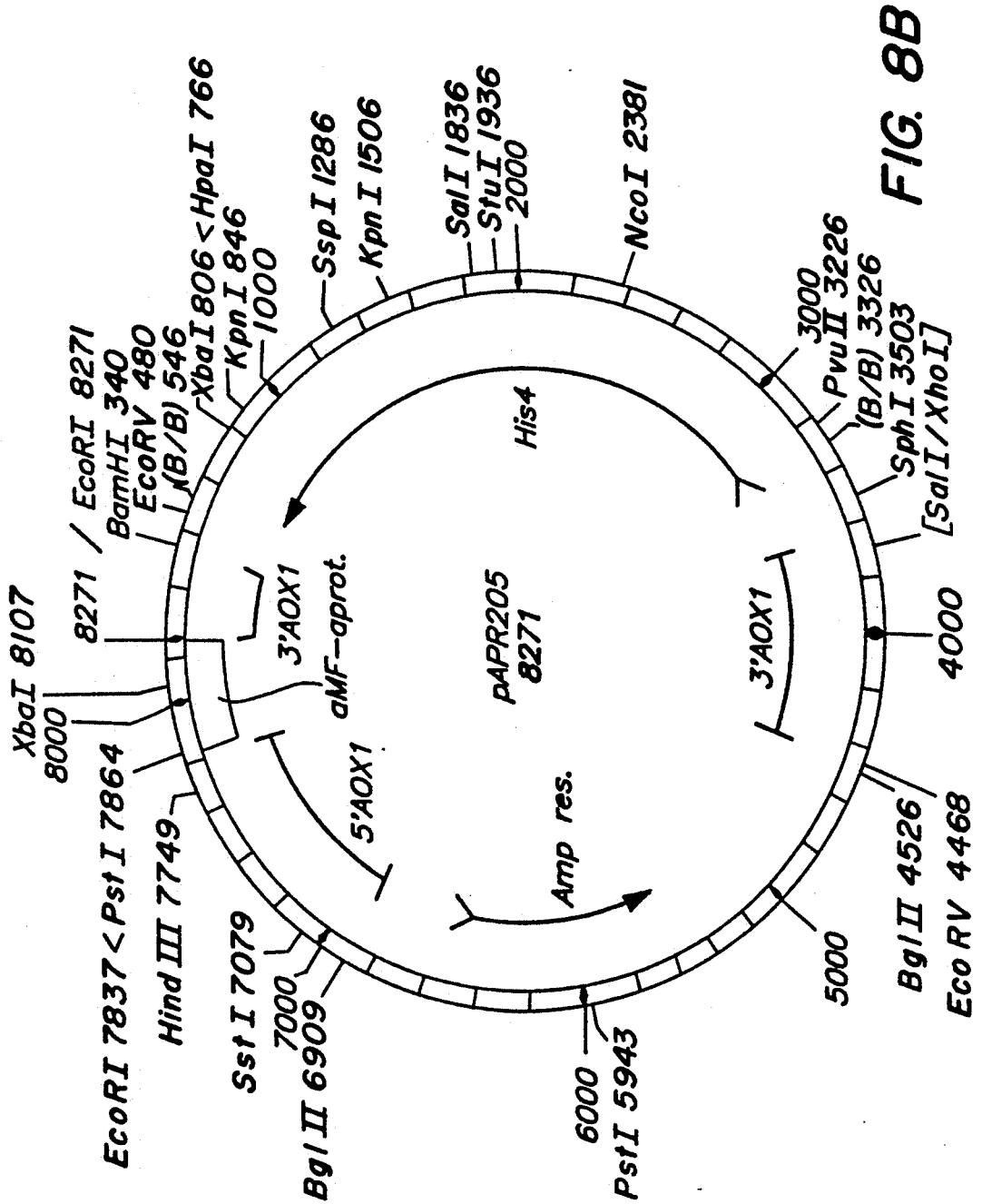

Alternatively, an aprotinin expression plasmid containing a wild-type αMF leader sequence fused to the synthetic aprotinin gene was constructed by way of a three-part ligation. 10.6 ng of the ~280 bp EcoRI-XbaI fragment of pAPR103 (which contains the αMF leader sequence fused in frame to the first 15 nucleotides of the aprotinin coding sequence) was ligated to 19.6 ng of the ~500 bp XbaI-BamHI fragment of pAPR105, (which contains most of the aprotinin gene and the AOX1 terminator), and 180 ng of the ~7500 bp EcoRI-BamHI vector fragment from pAO815 (molar ratios of pAO815 fragment:αMF insert:APR insert is 1:1.5:1.5). The ligation was transformed into MC1061 cells and Amp ® clones were selected. The αMF leader-aprotinin coding sequence of one of the resulting positives, pAPR205, was confirmed by sequencing. The restriction map of pAPR205 is identical to that of pAPR105, and is shown in FIG. 8B.

c. pAPR501

A vector comprised of five tandem head to tail repeats of the aprotinin expression cassette was constructed following the protocol of Cohen and Carmichael, 1986 (DNA 5: 339-343), wherein: 1) the cassette of interest is inserted in both orientations into a vector's polylinker region, 2) the insert is excised using different pairs of restriction enzymes, 3) fragments having cohesive termini are ligated, and the ligation is digested with an enzyme that cuts outside the desired multimer, 4) the multimer is isolated and cloned into the appropriate vector. This method was employed with the 1700 bp AOX1-aprotinin cassette from pAPR205.

The SacI site in pUC19 was converted into a BolII site to prepare the polylinker site already present in pUC19 to receive the aprotinin expression cassette. The conversion was accomplished using an oligonucleotide of the following sequence: 5' AGATCTAGCT 3' which was self-annealed and ligated with SacI-digested PUC19 DNA in a ratio of 11 pmoles of pUC19 to 1 nmole of oligo. The ligation mixture was digested with BglII and the linearized, approximately 2700 bp vector fragment was isolated with DE-81 paper and EtOH precipitated. The redissolved DNA (~4 μg) was digested once more with BglII, phenol extracted, and EtOH precipitated. 250 ng of the redissolved DNA was ligated to itself in a volume of 50 μl, and 20 ng was transformed into JM103. Miniprep DNA was digested with SacI and BolII, and a clone containing a 944 bp fragment was named pUCI 9-SacI+BglII. The polylinker of pUCI 9-SacI+BglII has the structure:

5'EcoRI-BglII-KpnI-SmaI-BamHT-XbaI-SalI-PstI-SphI-HindIII 3'

Plasmid pAPR205, which contains a single copy of the AOX1 promoter-preproαMF-aprotinin-AOX1 terminator was digested with BamHI and BolII to release the expression cassette on a 1.7 Kb DNA fragment. The 1.7 Kb fragment was isolated using DE81 paper. 200 ng of insert were ligated to 100 ng of BamHI-cut pUC19-SacI+BglII. The ligation was transformed into MC1061 cells and Amp ® colonies were selected. Plasmids containing the aprotinin insert in the sense orientation (with respect to the lacZ gene of pUC19) were identified by the 926 bp sized band evident after digestion with BamHI and SacI. One of these was called pAPR401. Similarly, plasmids containing the insert in the antisense orientation were identified by the 2628 bp sized band evident after digestion with the same enzymes. One of these was called pAPR402.

To construct in vitro a DNA fragment which contained four tandemly repeated copies of the aprotinin expression cassette, the following scheme was employed. Plasmid pAPR401 was digested with SalI and KonI or SohI and BglII. Plasmid pAPR402 was digested with BglII and SalI or KonI and SohI. The enzymes EcoRI, XbaI, PstI, and HindIII were not used because their sites also occur within the 1700 bp expression cassette. BamHI also was not used because it occurs only at the 3' end of the insert in both plasmids.

The double digests were each separated on a 0.8% agarose gel and the 1700 bp fragment eluted with DE81 paper. One microgram of each of the four fragments was combined together with the other fragments and the mix was ligated in a 20 μl ligation mixture. It was anticipated that ligations would occur between the fragments having compatible ends, i.e., the BglII-SalI fragment from pAPR402 would ligate to the SalI-KpnI fragment from pAPR401, which would in turn ligate to the KpnI-SphI fragment from pAPR402, which would in turn ligate to the SphI-BplII fragment from pAPR401.

Four hundred nanograms of the ligation mix were separated on a 0.8% agarose gel. The majority of the DNA was found to be present as >10 Kb species, indicating that ligation had occurred. The mixture was heated to inactivate the ligase, digested to completion with BglII, and separated on a 0.8% agarose gel. The major species were dimer (3.4 Kb)>tetramer (6.8 Kb)>trimer (5.1 Kb)>monomer (1.7 Kb).

Figure 9:
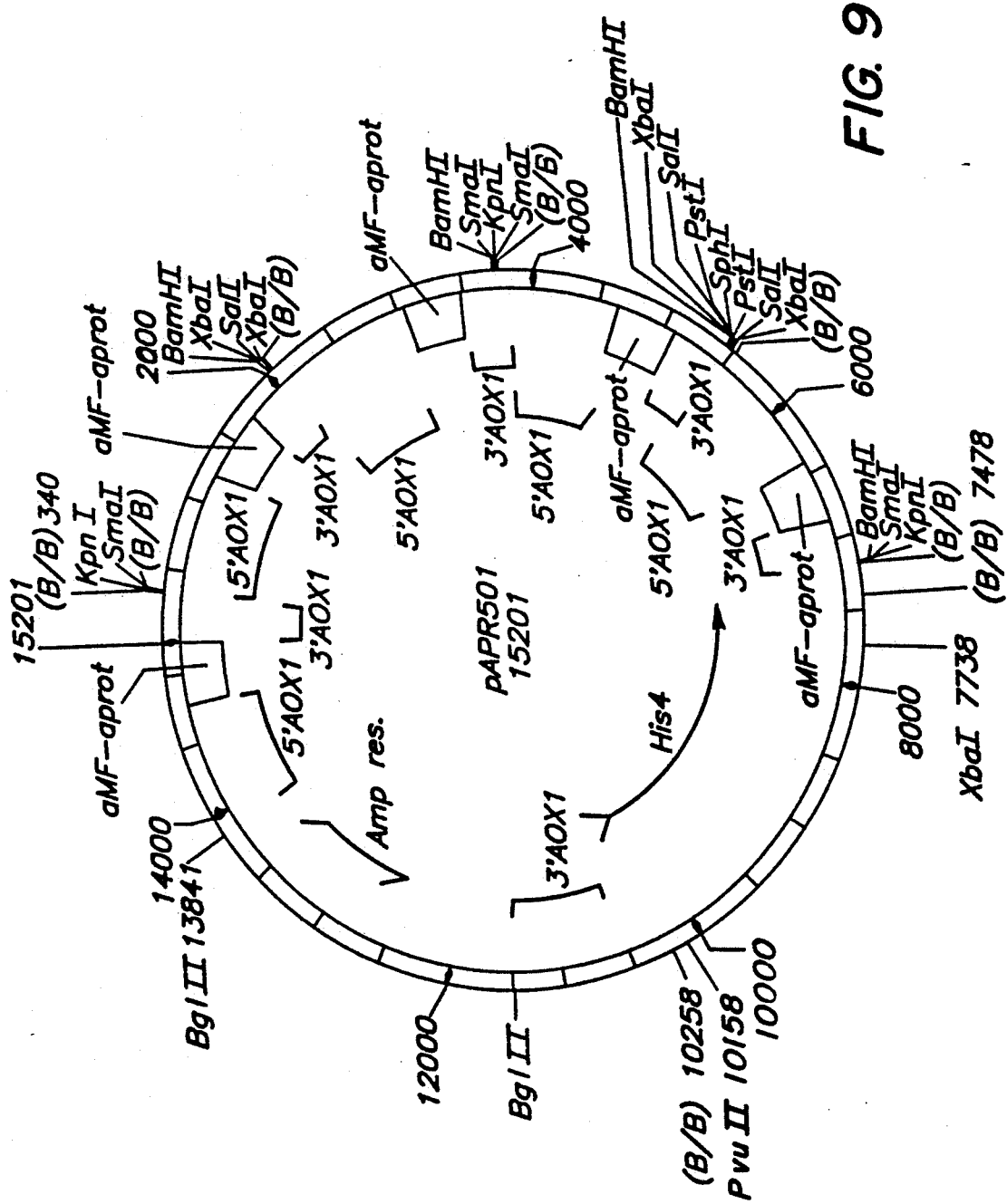
FIG. 9 is a restriction map of plasmid pAPR501.
Figure 10:
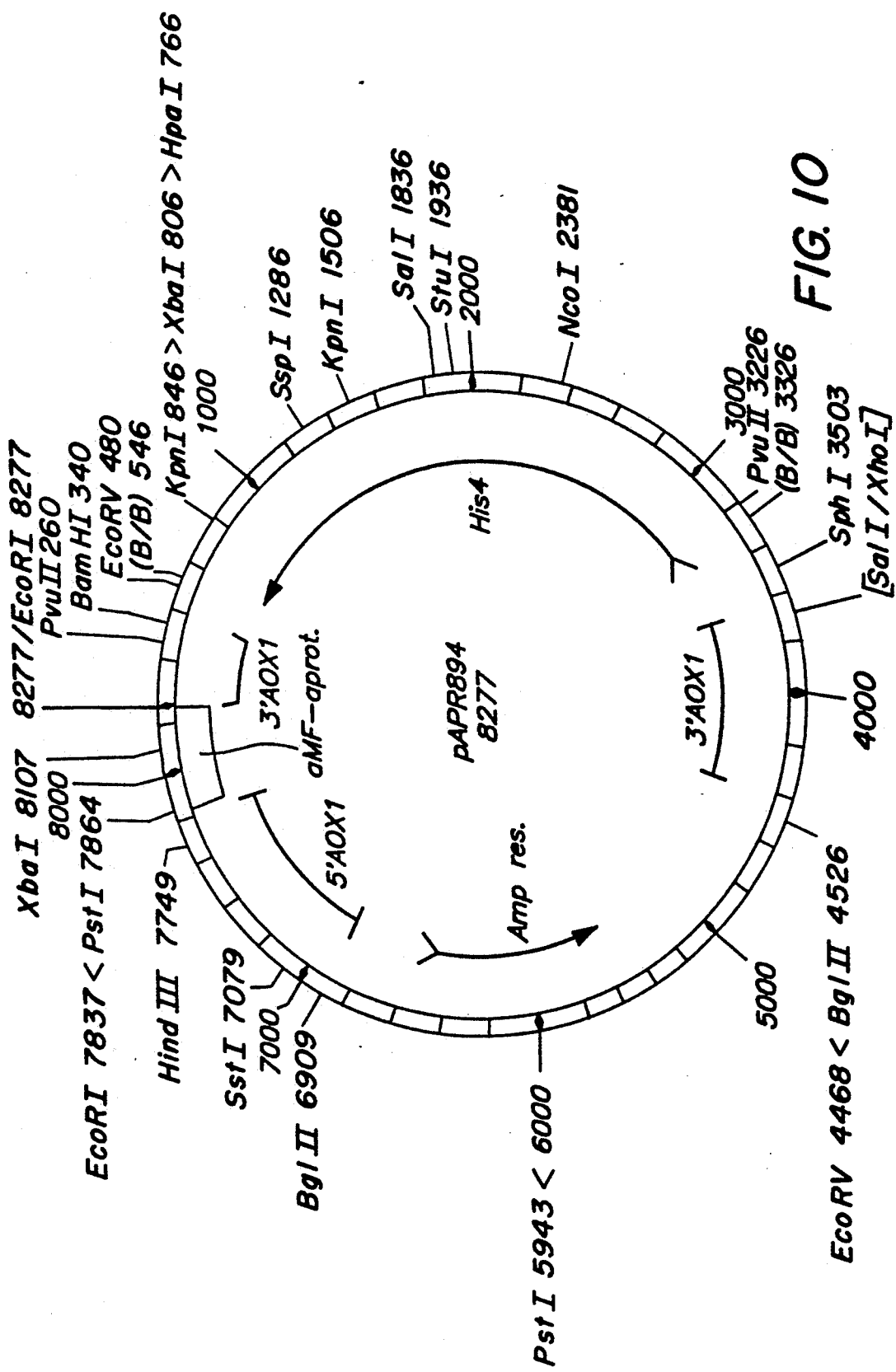
FIG. 10 is a restriction map of plasmid pAPR894.
Figure 11:
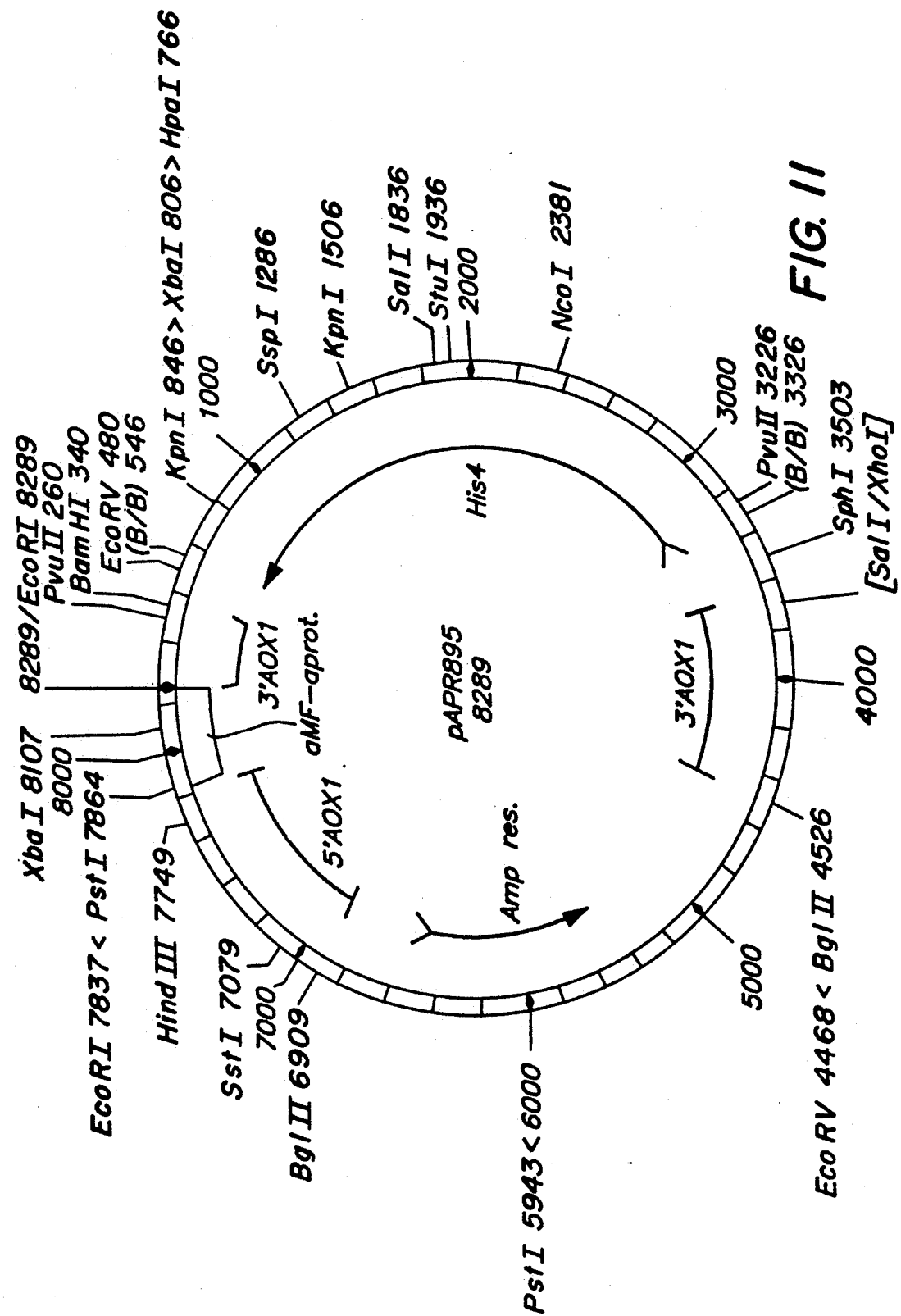
FIG. 11 is a restriction map of plasmid pAPR895.
Figure 12:
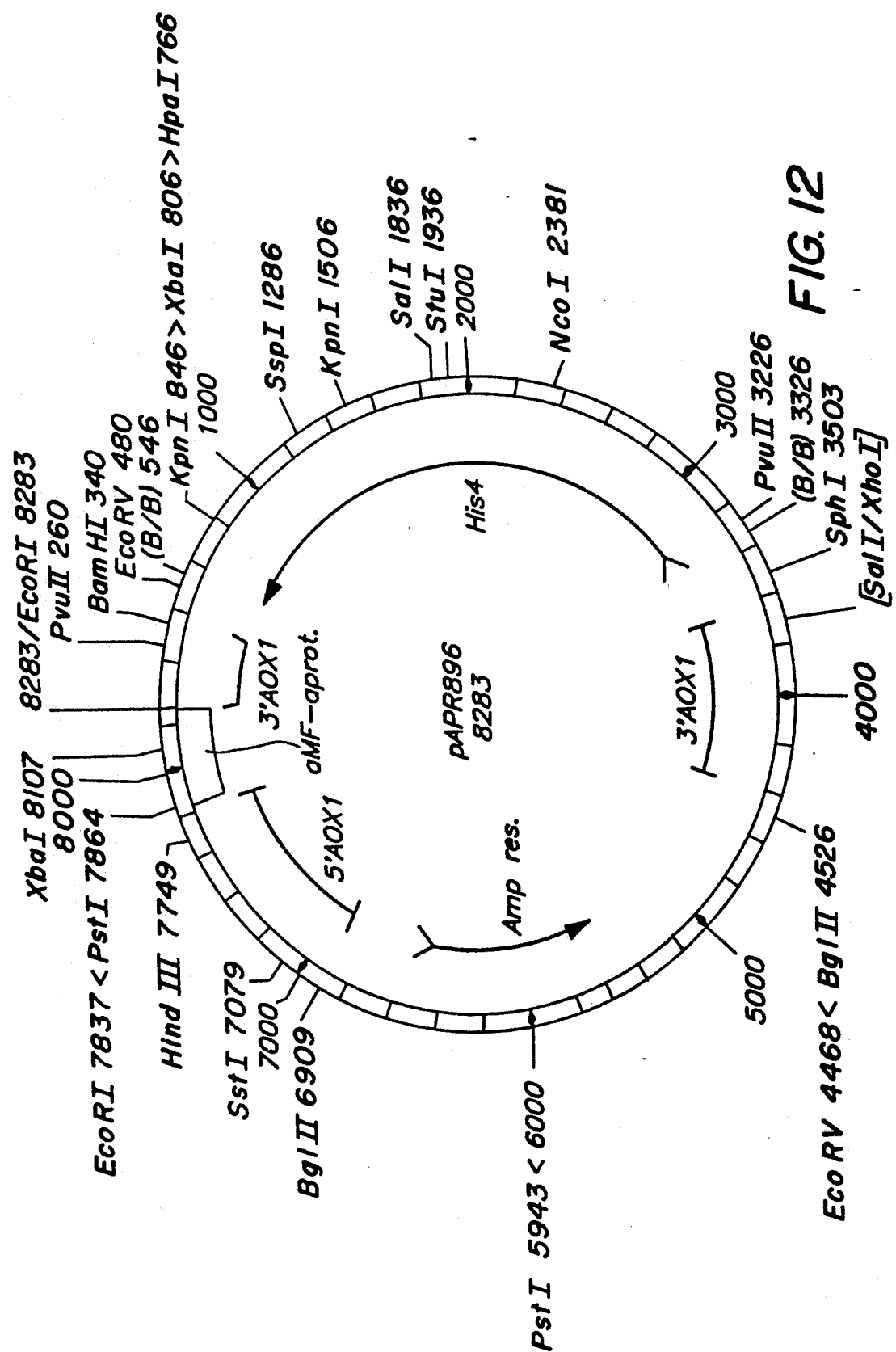
FIG. 12 is a restriction map of plasmid pAPR896.
Figure 13:
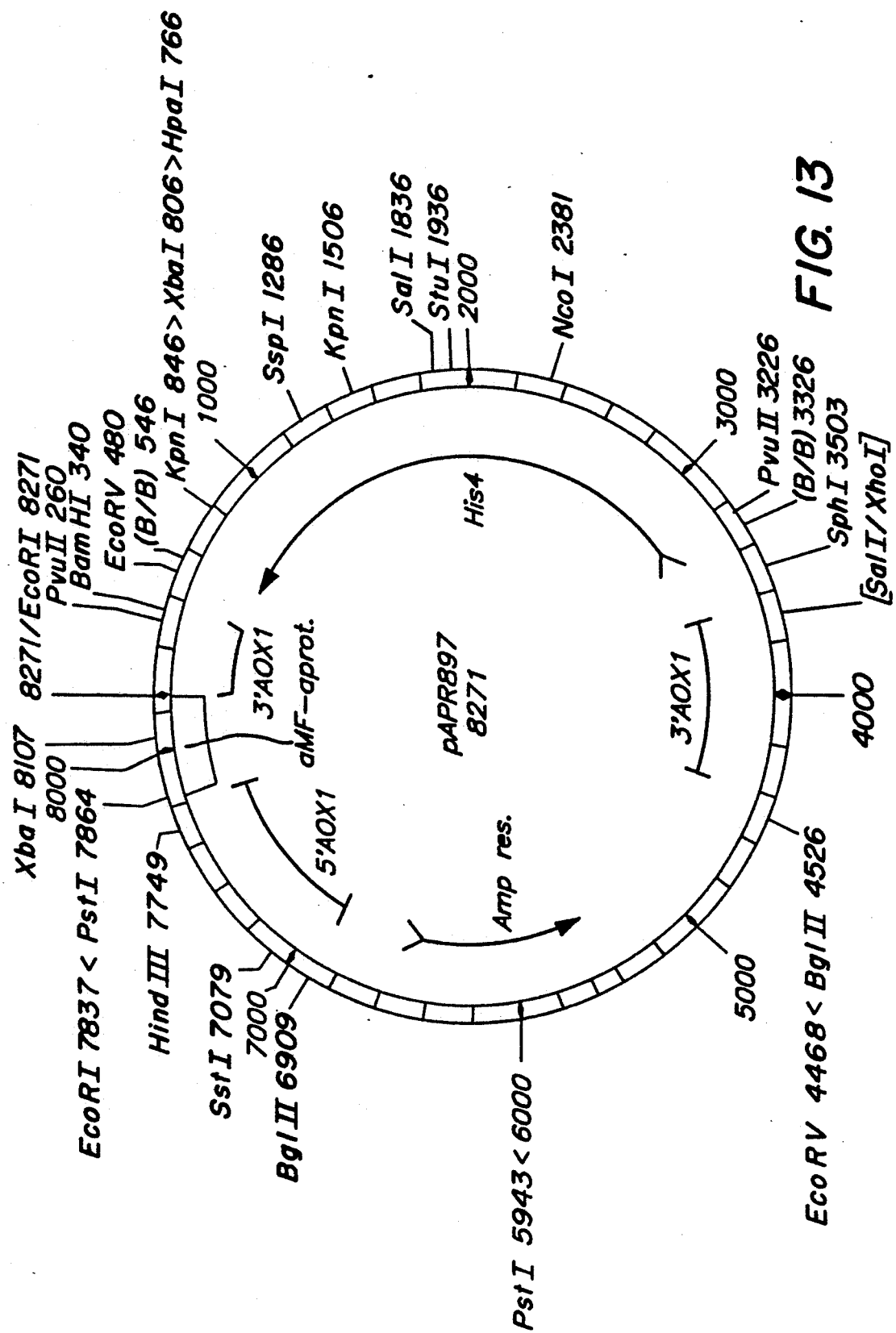
FIG. 13 is a restriction map of plasmid pAPR897.

The tetramer, comprised of four tandem repeats of the aprotinin expression cassette, was eluted with DE81 paper. 60 ng of tetramer was ligated with 50 ng of BamHI-cut pAPR205 (has one copy of aprotinin cassette). The ligation was transformed into MC1061 cells, and Amp ® colonies were selected. Plasmids containing five copies of the expression cassette were identified by the high intensity of ethidium bromide staining of the 1702 bp sized band evident upon digestion with SacI. One of these was called pAPR501 (FIG. 9).

d. pAPR894, pAPR895, pAPR896 and pAPR897

The 434 bp EcoRI fragment from pAPR205 (which encodes the AMF-lys-arg-aprotinin sequence) was isolated and 18 ng were ligated to 100 ng of EcoRI-digested M13mp19 (3 molar excess of insert to vector). The ligation was transformed into CJ236 cells and 24 plaques were selected. Correct plasmid was identified by the appearance of 680 and 437 bp bands upon digestion with BolII and PstI, respectively, and was called pAPR305. Plasmid pAPR305 served as template for four separate mutagenesis reactions with the following oligonucleotides:

| Oligo | Sequence | Modification of encoded protein |
| --- | --- | --- |
| 90-4 | TCTTTGGATAAAAGAGAGGCTAGACCTGACTTCTGT | adds (Glu—Ala)$_1$ |
| 90-5 | TCTTTGGATAAAAGAGAGGCTGAAGCTGAAGCTAGACCTGACTTCTGT | adds (Glu—ala)$_3$ |
| 90-6 | TCTTTGGATAAAAGAGAGGCTGAAGCTAGACCTGACTTCTGT | adds (Glu—ala)$_2$ |
| 90-7 | TCTTTGGATAAAAGAAAACCTGACTTCTGT | R to K change |

The mutagenesis reactions involving oligos 90-4, 90-6 and 90-5 were designed to insert DNA sequences encoding one, two and three Glu-Ala dipeptides, respectively, between the AMF prepro-Lys-Arg and aprotinin-encoding sequences of the AMF prepro-Lys-Arg-aprotinin fusion gene. The mutagenesis reaction utilizing oligo 90-7 was designed to change the initial codon of the aprotinin gene coding sequence from Arg to Lys.

The mutagenesis products were used to transform E. coli strain JM103 and correctly mutagenized plasmids were identified by hybridization of specific probes to plaque lifts. The intermediate plasmids resulting from the mutagenesis reactions were verified by sequencing to be correct and were named as follows:

| oligio | Intermediate plasmid |
| --- | --- |
| 90-4 | pAPR904 |
| 90-5 | pAPR905 |

-continued

| oligio | Intermediate plasmid |
|---|---|
| 90-6 | pAPR906 |
| 90-7 | pAPR907 |

The EcoRI fragment was isolated from each of the four intermediate plasmids and a 3 molar excess of insert fragment to vector was ligated to 0.077 pmole EcoRI-digested phosphatase-treated pAO815 (200 ng). The ligations were transformed into MC1061 cells and amp ® colonies were selected. Correct plasmid was identified by restriction mapping,, as described below, and verified by sequencing to be correct:

| intermediate plasmids | restriction enzymes | band sizes | expression vector |
|---|---|---|---|
| pAPR904 | XbaI + HindIII | 358 + ~970 | pAPR894 |
| pAPR905 | XbaI + HindIII | 358 + ~970 | pAPR895 |
| pAPR906 | XbaI + HindIII | 358 + ~970 | pAPR896 |
| pAPR907 | XbaI + HindIII | 358 + ~970 | pAPR897 |

These expression plasmids are shown in FIGS. 10, 11, 12 and 13, respectively.

Example 3

Development of Aprotinin-Expressing Strains of *P. pastoris*

The His⁻ *Pichia pastoris* strain GS115 (ATCC 20864) was used as the host for transformation with 10 μg of SacI-digested pAPR105, pAPR205, pAPR894, pAPR895, pAPR896, or pAPR897 by the whole cell LiCl method of transformation (See European Patent Application No. 312,934; also published as U.S. Pat. No. 4,929,555). His⁺ transformants of each type were selected and genomic analysis carried out by Southern hybridization. The genomic DNAs were digested with EcoRI and probed with a nick-translated sample of the same plasmid used for the transformation.

Characterizations of several of the resulting strains are summarized below:

| Strain Name | Vector Copy Number | Site of Integration |
|---|---|---|
| G+APR105S19 | one | AOX1 |
| G+APR105S21 | one | AOX1 |
| G+APR205S10 | two | AOX1 |
| G+APR205S5 | one | AOX1 |

| Strain Name | Vector Copy Number | Modification Relative to Preceding Strains |
|---|---|---|
| G+APR894-12 | 1 c at AOX1 | glu—ala |
| G+APR895-14 | 1 c at AOX1 | (glu—ala)$_3$ |
| G+APR896-37 | 1 c at AOX1 | (glu—ala)$_2$ |
| G+APR897-28 | 1 c at AOX1 | arg changed to lys |

In addition, ten micrograms of the multiple copy expression cassette containing plasmid pAPR501 were digested with StuI and used to transform GS115 by the LiCl protocol. Twelve individual His⁺ transformants were chosen and genomic DNA prepared from YPD cultures of each. The DNA was digested with EcoRI, electrophoresed, blotted to nitrocellulose, and probed with nick-translated pAPR205. Eight of the His⁺ transformants (G+APR501S-1, 3, 5, 6, 8, 9, 11, and 12) showed the expected pattern of EcoRI fragments (1.3 Kb and 0.4 Kb) for integration of pAPR501 at the HIS4 locus. In addition, each of these DNAs also showed a 1.7 Kb species representing the expression cassette, which resulted from incomplete EcoRI digestion of the DNA. Two other transformants (2 and 7) were disrupted at the HIS4 locus but did not contain the expected EcoRI fragments, and additional transformants were not disrupted at HIS4 and showed no evidence of pAPR501 DNA integration elsewhere in the genome.

Northern blot analysis was then performed on total RNA extracted from methanol-grown cultures of the 12 transformants. Ten micrograms of each RNA prep were blotted to nitrocellulose and probed with an oligomer which hybridizes to AOX1 5' untranslated sequences present in the expression cassette. Total RNA from single-copy (strain G+APR205S5) and two-copy (strain G+APR205S10) aprotinin-expressing strains was included as both size and abundance controls. Each of the strains carrying the five-copy plasmid expressed a much greater amount of aprotinin-specific mRNA than did either the single- or two-copy strain. Further, the ratio of aprotinin mRNA:AOX1 mRNA also was much greater for the five-copy strains.

EXAMPLE 4

Fermentation of Strains

Media employed in fermentations described herein had the following compositions:

| Chemical | Grams/liter |
|---|---|
| A. 10× BASAL SALTS | |
| Phosphoric acid, 85% | 42.0 ml |
| Calcium Sulfate.2H2O | 1.8 |
| Potassium Sulfate | 28.6 |
| Magnesium Sulfate.7H2O | 23.4 |
| Potassium Hydroxide | 6.5 |
| B. PTM$_1$ TRACE SALTS | |
| Cupric Sulfate.5H2O | 6.0 |
| Sodium Iodide | 0.08 |
| Manganese Sulfate.H2O | 3.0 |
| Sodium Molybdate.2H2O | 0.2 |
| Boric Acid | 0.02 |
| Cobalt Chloride | 0.5 |
| Zinc Chloride | 20.0 |
| Ferrous Sulfate.7H2O | 65.0 |
| Biotin | 0.20 |
| Sulfuric Acid | 5.0 ml |

Strains G+APR105S19, G+APR105S21, G+APR205S10, G+APR205S5, G+APR501S3, G+APR894-12, G+APR895-14, G+APR896-37 and G+APR897-28 were analyzed in one-liter fermentors, runs 681, 682, 696, 697, 750, 730, 731, 732 and 733, respectively. The one-liter fermentations were conducted as follows:

The fermentors were autoclaved with one liter of medium containing 500 ml of 10X basal salts, 5% glycerol, and the remainder deionized water. After cooling, 3 ml of PTM$_1$ trace salts were added and the pH was adjusted to between 4 and 5 by adding NH$_4$OH. During the fermentations, NH$_4$OH again was used to maintain the pH and also as a nitrogen source. Strucktol J673 antifoam (Strucktol Co., Stow, Ohio) was used to control foaming; the temperature was controlled at 30° C.; and the agitation was adjusted to maintain the dissolved oxygen concentration above 20% of air saturation.

The batched fermentors were inoculated with 10 to 20 ml inoculum and the cell mass was allowed to increase until the glycerol was exhausted. After glycerol exhaustion, a feed of glycerol was started at 15 ml/h, and was fed for four to five hours to depress the enzymes in the methanol pathway and further increase cell density. When the glycerol feed ended, a methanol feed was initiated at 4 ml/h (for runs 681, 682, 696, 697 and 750; 2 ml/h for runs 730, 731, 732 and 733) to induce production of aprotinin. After 10–12 h at 4 ml/h initial feed rate (runs 681, 682, 696, 697 and 750), the methanol feed rate was increased, to 7 ml/h in runs 681 and 682; to 5 ml/h in runs 696 and 697; and to 6 ml/h in run 750. After 3 h at 2 ml/h initial feed rate (runs 730, 731, 732 and 733), the methanol feed rate was increased to 6 ml/h.

The run 681 and 682 fermentations were harvested after 60 h induction at the higher methanol feed rate; the run 696 and 697 fermentations were harvested after 83 h of induction; the run 750 fermentations were harvested after 87 h of induction; and the run 730, 731, 732 and 733 fermentations were harvested after 130 h of induction. The final feed volume of methanol in all nine runs was approximately 400 ml.

The cell concentration over time and the aprotinin concentration over time for each of the abovedescribed nine runs is summarized in Table 1.

TABLE 1

Fermentation Results with APR-producing Strains

| Strain | Time on Stream, h | Cell Concen. g/l | APR Concen. mg/l |
|---|---|---|---|
| G+APR105S19 | 60 | 325 | 125 |
| G+APR105S21 | 60 | 350 | 138 |
| G+APR205S10 | 83 | 290 | 320 |
| G+APR205S5 | 83 | 320 | 143 |
| G+APR501S03 | 87 | 441 | 930 |
| G+APR894-12 | 130 | 304 | 143 |
| G+APR895-14 | 130 | 320 | 258 |
| G+APR896-37 | 130 | 343 | 157 |
| G+APR897-28 | 130 | 334 | 167 |

The data presented above clearly show that the productivity of the multi-APR encoding strain G+APR501S03 is several-fold greater than either the two-copy or one-copy strains. The yield continues to increase during the course of the fermentation, reaching a level of approximately 930 mg aprotinin per liter fermentation broth when the run is terminated. This result is consistent with a stably-integrated, multi-cassette plasmid.

EXAMPLE 5

Strain Analysis a. Development of Aprotinin Specific Antisera

Rabbits were immunized with aprotinin or with aprotinin conjugated to human alpha-globulin. The conjugated aprotinin was prepared as follows. Two milligrams of aprotinin dissolved in 1 ml of water were added to 6 mg of human alpha globulin (U.S. Biochemical Corp., Cleveland, Ohio) that had been dissolved in 4 mls of 0.1M ammonium acetate buffer, pH 7.0, in a glass bottle. The aprotinin container was rinsed with two aliquots of 0.5 ml ammonium acetate buffer and the liquid was added to the aprotinin/human alpha-globulin mixture. The protein and peptide were stirred continuously while 6 ml of 0.2% (w/v) glutaraldehyde in water were added slowly dropwise. This mixture was stirred continuously for 4 hours at room temperature. The reaction was stopped by dialysis against 0.9% sodium chloride solution to remove any excess glutaraldehyde. After dialysis, the sample was divided into 1.5 ml aliquots at a concentration of 250 μg aprotinin per ml.

The rabbits were injected with Freund's complete adjuvant plus either aprotinin (150 μg) or aprotinin conjugate (125 μg) prepared as described above. They were boosted approximately five weeks later with 50–75 μg of the same immunogen as before, in Freund's incomplete adjuvant. A second boost was given approximately two weeks after the first boost, with 50–75 μg of the same immunogen as before, in Freund's incomplete adjuvant. The first bleed was taken two weeks later. The rabbits were boosted three more times, as described above at intervals of four to seven weeks between boosts. The rabbits were bled approximately two weeks after every boost.

The pre- and post-immunization bleeds were separately reacted with aprotinin standard and native *Pichia* proteins that had been separated on a 15% SDS gel, and blotted to nitrocellulose. Antiserum No. 192 was of high titer and showed the lowest reactivity to native *Pichia* proteins. Antiserum No. 195 was then used to develop an aprotinin-specific radioimmunoassay (RIA).

b. Development of Aprotinin-Specific RIA

A standard RIA was developed to quantitate aprotinin production in the recombinant strains.

Aprotinin was iodinated by the following procedure. Six μg of aprotinin were combined with 1 mCi $^{125}$I-NaI in 10 μl 0.5M NaPO$_4$, pH 7.4. One microgram of chloramine T was measured and added to the aprotinin-iodine mixture. Bis-metabisulfide (2.5 μg) was added after the 30 sec incubation to quench the reaction. Fifty μg of crystalline bovine serum albumin (BSA) were added after the iodination reaction to act as a carrier throughout the remainder of the procedure. The solution was then removed to a CH Cyclohexyl Bondelute column (a silicia solid support having cyclohexyl groups attached thereto; high capacity material employed has a particle size of about 40 microns; available from Analytichem International, Harbor City, CA), washed with 0.1% aqueous trifluoroacetic acid (TFA), and eluted with 3.0 ml of a 50% 2-propanol/50% 0.1% TFA mixture. The elution fraction was dried in a Speedvac centrifuge under reduced pressure to a volume of 1.0 ml and was subsequently applied to a Vydac 218 TP C18 HPLC column (a silica solid support having an eighteen carbon chain covalently attached thereto; spherical particles are employed which have a particle size of about 5–10 microns and a 300 Angstrom pore size; available from Alltech Associates, Inc., Deerfield, Ill.). The HPLC column was run for 60 minutes at a flow rate of 1.0 ml/min, with a linear gradient of from 20 up to 100% acetonitrile in 0.1% TFA. A 10 μl aliquot of each fraction was counted, and trichloroacetic acid (TCA) precipitations were performed on the peak fractions. The iodination procedure is generally described in Hunter, W. M. and Greenwood, F. C. (1962), *Nature* 194: 495–496.

Ten to twelve thousand cpm each of fractions Nos. 10, 27, 36, and 45 were incubated for 20 hr at 4° C. in glass tubes in the presence or absence of 200 ng unlabeled aprotinin and with 1:100 and 1:500 dilutions of the antisera from four rabbits. The incubation mixture was precipitated with 100 μl of a 1:40 dilution of pansorbin, 2.0 ml wash buffer was added and centrifuged at 3200 rpm for 68 min. After decantation, the tubes were counted in a gamma counter. All antisera demonstrated specific binding of the void volume fraction (No. 10), but did not react specifically with any of the other fractions. Antisera from rabbit No.195, at a 1:500 working dilution, gave the most sensitive linear range, $ED_{80}=50$ ng.

The optimized aprotinin RIA used a working No. 195 antibody dilution of 1:20,000 (1:100,000 final in tube). The RIA has a sensitivity of 0.1 ng, a linear range measuring between 0.1 and 1.0 ng, with 36.0% of the $^{125}I$-aprotinin specifically bound. Nonspecific binding is approximately 2-3% of the total 10,000-12,000 cpms added.

c. Bioactivity Assay

The basis for analyzing the bioactivity of recombinant aprotinin was aprotinin-mediated inhibition of trypsin-mediated hydrolysis of benzoyl L-arginine p-nitroanalide. Upon hydrolysis, a distinct yellow chromophore is produced which can be monitored at 410 nm.

The assay was performed as follows:

1) Standard Curve

To each of nine eppendorf tubes is added 600 μl incubation buffer (50 mM Tris-HCl, pH 8.0, 10 mM $MgCl_2$, 10 mM $CaCl_2$) and 200 μl trypsin solution (100 enzyme units/ml incubation buffer). Each tube represents one point on the standard curve. Therefore, each tube receives from 0 to 200 μl aprotinin standard (0.112 mg/ml of incubation buffer) in 25 μl increments. Each 25 μl of aprotinin standard solution contains 2.8 μg of aprotinin. Deionized water is then added to bring the final volume in each tube to 1 ml.

The tubes are incubated at room temperature for 30 minutes, and then assayed for trypsin hydrolytic activity. To a quartz cuvette having a 1 cm path length is added 900 μl of incubation buffer and 50 μl of benzoyl L-arginine p-nitroanalide substrate (200 mM substrate in DMSO). The cuvette is incubated at room temperature for three minutes. Next, 50 μl of the aprotinin-trypsin solution in each of the eppendorf tubes is separately added to a cuvette and mixed by inversion. The absorbance is measured over five minutes ("time run" function in kinetics mode) in a UV-vis spectrophotometer which has been blanked against incubation buffer at 410 nm. A standard curve was generated from the 'rate of change' data obtained at each concentration of aprotinin.

2) Experimental Samples

The RIA was used to determine the concentration of antigenic aprotinin in the experimental samples. These values then were used to determine the volume of fermentor broth or purified product needed to fall within the linear range of the standard curve. The experimental samples were then assayed as described for the standard curve. Using the 'rate of change' value obtained for each experimental sample, and the aprotinin standard curve, the concentration of bioactive aprotinin was calculated.

d. Aprotinin Levels in Fermentor Samples

Fermentor broth samples from final time points for fermentor runs #681, 682, 696, 697, and 750, 730, 731, 732 and 733 were analyzed in the RIA and in the bioactivity assay. The results are summarized below:

| Run # | Activity Assay Bioactive Aprotinin (mg/L) | RIA Antigenic Aprotinin (mg/L) | % Bioactive |
|---|---|---|---|
| 681 | 114 | 125 | 91% |
| 682 | 142 | 138 | 103% |
| 696 | 324 | 320 | 101% |
| 697 | 143 | 143 | 100% |
| 750 | 825 | 930 | 89% |
| 730 | 84 | 143 | 59% |
| 731 | 214 | 248 | 83% |
| 732 | 183 | 157 | 117% |
| 733 | 143 | 167 | 86% |

The results of these analyses show that essentially 100% of the aprotinin molecules secreted into the fermentation media are bioactive.

e. Biochemical Isolation and Characterization of Aprotinin

1) Purification of Aprotinin

Aprotinin contained in 200 ml of fermentor broth, as a result of secretion into the broth by an aprotinin-secreting strain of *P. pastoris*, was purified to homogeneity as follows. 200 ml of thawed fermentation broth was combined with approximately 100 ml of 20 mM acetic acid buffer (pH 5.0, conductivity 5.20), to achieve a pH of 5.07 and a conductivity of 16.92 mMho in the diluted broth. The diluted broth was loaded onto an SP-60 capsule (Zeta-chrom SP-60 radial flow capsule; available from Western Analytical Products Co., Inc; manufactured by CUNO) at a flow rate of 3.3 ml/min. The capsule was activated according to manufacturer's instructions prior to loading. The non-binding fractions were conveniently collected in 50 ml aliquots although they can be collected as a single volume. The capsule was then washed with 100 ml of 20 mM acetic acid buffer. The wash fraction was collected in a single 50 ml aliquot, and then the bound material was eluted with a 200 ml linear gradient, from 0 to 1M, of NaCl in 20 mM acetic acid. The eluant was collected in 50 ml aliquots.

Samples of the non-binding fractions, wash fraction, and eluted fractions were analyzed for aprotinin content by RIA and SDS-PAGE. The tricine gel system was used exclusively for the SDS-PAGE characterizations of aprotinin containing fractions because of its capacity to resolve proteins in the low molecular weight region. The more mobile trailing ion, tricine, along with the separation of small proteins from SDS micelles in the stacker, enables this enhanced resolution. The gels used a 16% acrylamide separative region in conjunction with a 4% acrylamide stacking region. The recipes for the buffers used are shown below:

| Anode Buffer: | | |
|---|---|---|
| 0.2 M | Tris base | 24.22 g |
| → | Add 800 mls of deionized water | |
| → | Add 1 N HCl to pH 8.9 | |
| → | Add deionized water to 1000 mls | |
| Cathode Buffer: | | |
| 0.1 M | Tris | 12.11 g |
| 0.1 M | Tricine | 17.92 g |
| 0.1% (w/v) | SDS | 5 mls of 20% |
| → | Add deionized water to 1000 mls | |
| Gel Buffer: | | |
| 3.0 M | Tris | 72.67 g |
| 0.3% | SDS | 3 mls of 20% |
| → | Add 100 mls of deionized water | |
| → | Add 5 N HCl to pH 8.45 | |

-continued

→ Add deionized water to 200 mls

2) Characterization of Aporotinin

Aprotinin purified from run #696 by ion exchange chromatography was loaded onto the tricine gel system described in section (1) above. These gels were then electroblotted onto polyvinylidene difluoride (PVDF) immobilon as described previously [Matsudaira, P. T., 1987, *J. Biol. Chem.* 262:10025; Moos, M., et. al., *J. Biol Chem.* 263:6005 (1988)]. The gel was placed in CAPS transfer buffer (10 mM 3-[cyclohexylamino]-1-propanesulfonic acid, 10% methanol, pH 11.0) to equilibrate for 15 minutes before blotting. The PVDF membrane was pre-wetted in a small volume of 100% methanol for 1-2 seconds, then placed in transfer buffer for five minutes. The blotting cassette was assembled in the normal fashion with the PVDF membrane adjacent to the gel. The protein was transferred onto the membrane at 200 mA for 60 minutes.

Following transfer, the membrane was stained in Coomassie Blue stain for five minutes followed by rapid destain for 5-10 minutes. The band corresponding to aprotinin, identified by its parallel migration with an aprotinin standard, was cut from the immobilon filter and loaded directly into the sequencer. The protein sequence was determined on an Applied Biosystems 470A Gas Phase Protein Sequencer (Hunkapillar, M. W., and Hood, L. E., 1983, *Science* 219:650; Hewick, R. M., et. al., 1981, *J. Biol. Chem.* 256:7990).

The amino terminal sequence of purified protein from two different fermentations was determined and two different products were identified. The aprotinin secreted in Run 696, employing strain G+APR205S10, had the following sequence:

|  | 1 | 5 | 10 | 15 | 20 |
|---|---|---|---|---|---|
| Sequence Determined: | AKEEGVSLDKRRPDFCLEPPY... |
| Sequence Expected APROTININ: | RPDFCLEPPY... |

This strain produced an aprotinin analog which had 11 amino acids attached to the N-terminus of the authentic aprotinin molecule. These 11 amino acids are from the carboxy terminus of the AMF leader sequence.

Strain G+APR205S5, grown in Run 697, yielded a product at the end of its fermentation which was different than that characterized from Run 696. This aprotinin analog molecule had four AMF amino acids attached to the N-terminal end of aprotinin:

|  | 1 | 5 | 10 |
|---|---|---|---|
| Sequence Determined: | LDKRRPDFCLEPPY... |
| Sequence Expected APROTININ: | RPDFCLEPPY... |

The aprotinin analogs secreted by the strains grown in these fermentation runs showed 100% bioactivity, demonstrating that the additional sequences at the N-terminus of the molecule do not interfere with activity.

Broth from fermentation runs 730-733 was also separated on a preparative Tricine gel under reducing conditions. The samples were then transferred to Immobilon and stained with Coomassie blue to identify the protein in each broth sample that migrated similarly to the aprotinin standard. The band corresponding to the protein species that migrated closest to standard aprotinin in each broth sample was excised from the membrane and used in the determination of the N-terminal amino acid sequence of the protein.

The N-terminal protein sequences obtained for the major products of runs 730-733 were as follows:

| Run | Sequence Determined |
|---|---|
| 730 | EA-RPDFCLEPPY |
| 731 | EAEAEA-RPDFCLEPPY |
| 732 | EAEA-RPDFCLEPPY |
| 733 | KR-KPDFCLEPPY |

The addition of glu-ala sequence(s) (runs 730, 731 and 732) allowed for correct processing at the preceding lys-arg site, while one or more glu-ala residues remain at the N-terminus of the APR product. Regardless of the presence or absence of additional amino acids at the N-terminus of APR, all compounds prepared and described herein are seen to be highly bioactive (see Table in section 5d above).

EXAMPLE 6

Construction of Plasmid pAMF101

The AMF pre-pro sequence was isolated from M13mp19αMF by digesting with EcoRI and BamHI and isolating the about 267 bp fragment on a 1.3% agarose gel. To prepare plasmid M13mp19αMF, 15 μg of plasmid pAO208 (the construction of which is described hereinafter) were digested with HindIII, filled in with Klenow-fragment DNA polymerase, and digested with EcoRI. The digestion was run on a 1.7% agarose gel and the 267 bp fragment comprised of the AMF pre-pro sequence was isolated.

10 μg of M13mp19 were digested with SmaI and EcoRI and the large, about 7240 bp plasmid fragment was isolated on a 0.8% agarose gel. The plasmid fragment and the 267 bp fragment containing the AMF pre-pro sequence (including the proteolytic processing site: lys-arg) were ligated together by T4 DNA ligase. The M13mp19-AMF pre-pro sequence ligation mixture was then transformed into JM103 cells and DNA from the plaque was characterized. The correct plasmid was called M13mp19αMF.

Twenty-five nanograms of the EcoRI-BamHI fragment of M13mp19αMF were ligated to 100 ng of pI-BI25 previously cut with EcoRI and BamHI, and the ligation products were transformed into MCI061 cells. Amp ® colonies were selected and the correct plasmid was identified by digestion with EcoRI and BamHI. The correct plasmid demonstrated a 260 bp band, and was called pAMFI01 (see FIG. 3).

Construction of Plasmid -pAO208

The AOX1 transcription terminator was isolated from 20 μg of pPG2.0 [pPG2.0=BamHI-HindIII fragment of pG4.0 (NRRL 15868)+pBR322] by StuI digestion followed by the addition of 0.2 μg SalI linkers (GGTCGACC). The plasmid was subsequently digested with HindIII and the 350 bp fragment isolated from a 10% acrylamide gel and subcloned into pUC18 (Boehringer Mannheim) digested with HindIII and SalI. The ligation mix was transformed into JM103 cells (that are widely available) and Amp ® colonies were selected. The correct construction was verified by HindIII and SalI digestion, which yielded a 350 bp fragment, and was called pA0201.

5 μg of pA0201 was digested with HindIII, filled in using *E. coli* DNA Polymerase I Klenow fragment, and 0.1 μg of BglII linkers (GAGATCTC) were added. After digestion of the excess BglII linkers, the plasmid was reclosed and transformed into MC1061 cells. Amp®  cells were selected, DNA was prepared, and the correct plasmid was verified by BglII, SalI double digests, yielding a 350 bp fragment, and by a HindIII digest to show loss of HindIII site. This plasmid was called pA0202.

An alpha factor-GRF fusion was isolated as a 360 bp BamHI-PstI partial digest from pYSV201. Plasmid pYSV201 is the EcoRI-BamHI fragment of GRF-E-3 inserted into M13mp18 (New England Biolabs). Plasmid GRF-E-3 is described in European Patent Application No. 206,783. 20 μg of pYSV201 plasmid was digested with BamHI and partially digested with PstI. To this partial digest was added the following oligonucleotides:

5'AATTCGATGAGATTTCCTTCAATTTT-
TACTGCA 3'

3'GCTACTCTAAAGGAAGTTAAAAATG 5'.

Only the antisense strand of the oligonucleotide was kinase labelled so that the oligonucleotides did not polymerize at the 5'- end. After acrylamide gel electrophoresis (10%), the fragment of 385 bp was isolated by electroelution. This EcoRI- BamHI fragment of 385 bp was cloned into pA0202 which had been cut with EcoRI and BamHI. Routinely, 5 ng of vector cut with the appropriate enzymes and treated with calf intestine alkaline phosphatase, was ligated with 50 ng of the insert fragment. MC1061 cells were transformed, Amp® cells were selected, and DNA was prepared. In this case, the resulting plasmid, pA0203, was cut with EcoRI and BglII to yield a fragment of greater than 700 bp. The α-factor GRF fragment codes for the (1-40)leu$^{27}$; version of GRF and contains the processing sites lys-arg-glu-ala-glu-ala.

The AOX1 promoter was isolated as a 1900 bp EcoRI fragment from 20 μg of pAOP3 and subcloned into EcoRI-digested pA0203. The development of pAOP3 is disclosed in European Patent Application No. 226,846 and described hereinbelow. MC1061 cells were transformed with the ligation reaction, Amp® colonies were selected, and DNA was prepared. The correct orientation contains a ≈376 bp HindTTT fragment, whereas the wrong orientation has an ≈675 bp fragment. One such transformant was isolated and was called pA0204.

The parent vector for pA0208 is the HIS4, PARS2 plasmid pYJ32 (NRRL B-15891) which was modified to change the EcoRV site in the tet® gene to a BglII site, by digesting PYJ32 with EcoRV and adding BglII linkers to create pYJ32(+BglII). This plasmid was digested with BglII and the 1.75 Kb BglII fragment from pA0204 containing the AOX1 promoter-α mating factor-GRF-AOX1 3' expression cassette was inserted. The resulting vector was called pA0208. An EcoRI digest of pAO208 yielded an 850 bp fragment+vector, while vector having the other orientation yielded a 1.1 Kb fragment+vector.

Construction of Plasmid pAOP3

1. Plasmid pPG2.5 [a pBR322 based plasmid containing the approximately 2.5 Kbp EcoRI-SalI fragment from plasmid pPG4.0, which plasmid contains the primary alcohol oxidase gene (AOX1) and regulatory regions and which is available in an *E. coli* host from the Northern Regional Research Center of the United States Department of Agriculture in Peoria, Illinois as NRRL B-15868] was linearized with BamHI.

2. The linearized plasmid was digested with BAL31;

3. The resulting DNA was treated with *E. coli* DNA Polymerase I Klenow fragment to enhance blunt ends, and ligated to EcoRI linkers;

4. The ligation products were transformed into *E. coli* strain MM294;

5. Transformants were screened by the colony hybridization technique using a synthetic oligonucleotide having the following sequence:

5'-TTATTCGAAACGGGAATTCC-3'.

This oligonucleotide contains the AOX1 promoter sequence up to, but not including, the ATG initiation codon, fused to the sequence of the EcoRI linker;

6. Positive clones were sequenced by the Maxam-Gilbert technique. All three positives had the following sequence:

5'... TTATTCGAAACGAGGAATTCC ... 3'.

They all retained the "A" of the ATC (underline in the above sequence). It was decided that this A would probably not be detrimental; thus all subsequent clones are derivatives of these positive clones. These clones have been given the laboratory designation pAOPI, pAOP2 and pAOP3, respectively.

EXAMPLE 7

Construction of Plasmid PAO815

Plasmid pA0815 was constructed by mutagenizing plasmid pA0807 (which was in turn prepared as described hereinbelow) to change the ClaI site downstream of the AOX1 transcription terminator in pA0807 to a BamHI site. The oligonucleotide used for mutagenizing pA0807 had the following sequence:

5'-GAC GTT CGT TTG TGC GGA TCC AAT
GCG GTA GTT TAT-3'.

The mutagenized plasmid was called pA0807-Bam. Plasmid pA0804 was digested with BolII and 25 ng of the 2400 bp fragment were ligated to 250 ng of the 5400 bp BolII fragment from BglII-digested pA0807-Bam. The ligation mix was transformed into MC1061 cells and the correct construct was verified by digestion with PstI/BamHI to identify 6100 and 2100 bp sized bands. The correct construct was called pA0815. The restriction map of the expression vector pA0815 is shown in FIG. 7.

Construction of Plasmid pA0807

1. Preparation of fl-ori DNA:

fl bacteriophage DNA (50 μg) was digested with 50 units of RsaI and DraI (according to manufacturer's directions) to release the ≈458 bp DNA fragment containing the fl origin of replication (ori). The digestion mixture was extracted with an equal volume of phenol:

chloroform (V/V) followed by extracting the aqueous layer with an equal volume of chloroform and finally the DNA in the aqueous phase was precipitated by adjusting the NaCl concentration to 0.2M and adding 2.5 volumes of absolute ethanol. The mixture was allowed to stand on ice (4° C.) for 10 minutes and the DNA precipitate was collected by centrifugation for 30 minutes at 10,000×g in a microfuge at 4° C.

The DNA pellet was washed 2 times with 70% aqueous ethanol. The washed pellet was vacuum dried and dissolved in 25 μl of TE buffer [1.0 mM EDTA in 0.01M (pH 7.4) Tris buffer]. This DNA was electrophoresed on 1.5% agarose gel and the gel portion containing the ~458 bp fl-ori fragment was excised out and the DNA in the gel was electroeluted onto DE81 (Whatman) paper and eluted from the paper in 1M NaCl. The DNA solution was precipitated as detailed above and the DNA precipitate was dissolved in 25 μl of TE buffer (fl-ori fragment).

2. Cloning of Fl-ori into DraI Sites of pBR322 pBR322 (2 μg) was partially digested with 2 units DraI (according to manufacturer's instructions). The reaction was terminated by phenol:chloroform extraction followed by precipitation of DNA as detailed in step 1 above. The DNA pellet was dissolved in 20 μl of TE buffer. About 100 ng of this DNA was ligated with 100 ng of fl-ori fragment (step 1) in 20 μl of ligation buffer by incubating at 14° C. for overnight with 1 unit of T4 DNA ligase. The ligation was terminated by heating to 70° C. for 10 minutes and then used to transform E. coli strain JM103 [Janisch-Perron et al., Gene 22: 103(1983)]. Amp ®  transformants were pooled and superinfected with helper phage R408 [Russel et al., suora]. Single stranded phage were isolated from the media and used to reinfect JM103. Amp ®  transformants contained pBRfl-ori which contains fl-ori cloned into the DraI sites (nucleotide positions 3232 and 3251) of pBR322.

3 Construction of Plasmid PAO807 pBRfl-ori (10 μg) was digested for 4 hours at 37° C. with 10 units each of PstI and NdeI. The digested DNA was phenol:chloroform extracted, precipitated and dissolved in 25 μl of TE buffer as detailed in step 1 above. This material was electrophoresed on a 1.2% agarose gel and the NdeI - PstI fragment (approximately 0.8 kb) containing the fl-ori was isolated and dissolved in 20 μl of TE buffer as detailed in step 1 above. About 100 ng of this DNA was mixed with 100 ng of pA0804 (which was in turn prepared as described hereinbelow) that had been digested with PstI and NdeI and phosphatase-treated. This mixture was ligated in 20 μl of ligation buffer by incubating overnight at 14° C. with 1 unit of T4 DNA ligase. The ligation reaction was terminated by heating at 70° C. for 10 minutes. This DNA was used to transform E. coli strain JM103 to obtain pA0807.

Construction of Plasmid pA0804

Plasmid pA0804 has been described in PCT Application No. WO 89/04320. Construction of this plasmid involved the following steps: Plasmid pBR322 was modified as follows to eliminate the EcoRI site and insert a BolII site into the PvuII site:

pBR322 was digested with EcoRI, the protruding ends were filled in with Klenow Fragment of E. coli DNA polymerase I, and the resulting DNA was recircularized using T4 ligase. The recircularized DNA was used to transform E. coli MC1061 to ampicillin-resistance and transformants were screened for having a plasmid of about 4.37 kbp in size without an EcoRI site. One such transformant was selected and cultured to yield a plasmid, designated pBR322ΔRI, which is pBR322 with the EcoRI site replaced with the sequence:

5'-GAATTAATTC-3'

3'-CTTAATTAAG-5'.

pBR322ΔRI was digested with PvuII, and the linker having the sequence:

5'-CAGATCTG-3'

3'-GTCTAGAC-5' was ligated to the resulting blunt ends employing T4 ligase. The resulting DNAs were recircularized, also with T4 ligase, and then digested with BglII and again recircularized using T4 ligase to eliminate multiple BglII sites due to ligation of more than one linker to the PvuII-cleaved pBR322ΔRI. The DNAs, treated to eliminate multiple BglII sites, were used to transform E. coli MC1061to ampicillin resistance. Transformants were screened for a plasmid of about 4.38 kbp with a BglII site. One such transformant was selected and cultured to yield a plasmid, designated pBR322ΔRIBGL, for further work. Plasmid pBR322ΔRIBGL is the same as pBR322ΔRI except that pBR322ΔRIBGL has the sequence

5'-CAGCAGATCTGCTG-3'

3'-GTCGTCTAGACGAC-5' in place of the PvuII site in pBR322ΔRI.

pBR322ΔRIBGL was digested with a SalI and BglII and the large fragment (approximately 2.97 kbp) was isolated. Plasmid pBSAGI5I, which is described in European Patent Application Publication No. 0 226 752, was digested completely with BglII and XhoI and an approximately 850 bp fragment from a region of the P. pastoris AOX1 locus downstream from the AOX1 gene transcription terminator (relative to the direction of transcription from the AOX1 promoter) was isolated. The BglII-XhoI fragment from pBSAGI5I and the approximately 2.97 kbp, SalI-BglII fragment from pBR322ΔRIBGL were combined and subjected to ligation with T4 ligase. The ligation mixture was used to transform E. coli MC1061 to ampicillin resistance and transformants were screened for a plasmid of the expected size (approximately 3.8 kbp) with a BglII site. This plasmid was designated pA0801. The overhanging end of the SalI site from the pBR322ΔRIBGL fragment was ligated to the overhanging end of the XhoI site on the 850 bp pBSAGI5I fragment and, in the process, both the SalI site and the XhoI site in pA0801 were eliminated.

pBSAGI5I was then digested with ClaI and the approximately 2.0 kbp fragment was isolated. The 2.0 kbp fragment has an approximately 1.0-kbp segment which comprises the P. pastoris AOX1 promoter and transcription initiation site, an approximately 700 bp segment encoding the hepatitis B virus surface antigen ("HBsAg") and an approximately 300 bp segment which comprises the P. pastoris AOX1 gene polyadenylation signal and site-encoding segments and transcription terminator. The HBsAg coding segment of the 2.0 kbp fragment is terminated, at the end adjacent the 1.0 kbp segment with the AOX1 promoter, with an EcoRI site and, at the end adjacent the 300 bp segment with the AOX1 transcription terminator, with a StuI site, and has its subsegment which codes for HBsAg oriented and positioned, with respect to the 1.0 kbp promoter-containing and 300 bp transcription terminator-containing segments, operatively for expression of the HBsAg upon transcription from the AOX1 promoter. The EcoRI site joining the promoter segment to the HBsAg coding segment occurs just upstream (with respect to the direction of transcription from the AOX1 promoter) from the translation initiation signal-encoding triplet of the AOX1 promoter.

For more details on the promoter and terminator segments of the 2.0 kbp, ClaI-site-terminated fragment of pBSAGI5I, see European Patent Application Publication No. 226,846 and Ellis et al., Mol. Cell Biol. 5, 1111 (1985).

Plasmid pA0801 was cut with ClaI and combined for ligation using T4 ligase with the approximately 2.0 kbp ClaI-site-terminated fragment from pBSAGI5I. The ligation mixture was used to transform E. coli MC1061 to ampicillin resistance, and transformants were screened for a plasmid of the expected size (approximately 5.8 kbp) which, on digestion with ClaI and BglII, yielded fragments of about 2.32 kbp (with the origin of replication and ampicillin resistance gene from pBR322) and about 1.9 kbp, 1.48 kbp, and 100 bp. On digestion with BglII and EcoRI, the plasmid yielded an approximately 2.48 kbp fragment with the 300 bp terminator segment from the AOX1 gene and the HBsAg coding segment, a fragment of about 900 bp containing the segment from upstream of the AOX1 protein encoding segment of the AOX1 gene in the AOX1 locus, and a fragment of about 2.42 kbp containing the origin of replication and ampicillin resistance gene from pBR322 and an approximately 100 bp ClaI-BglII segment of the AOX1 locus (further upstream from the AOX1 -encoding segment than the first mentioned 900 bp EcoRI-BolII segment). Such a plasmid had the ClaI fragment from pBSAGI5I in the desired orientation, in the opposite undesired orientation, there would be EcoRI-BolII fragments of about 3.3 kbp, 2.38 kbp and 900 bp.

One of the transformants harboring the desired plasmid, designated pA0802, was selected for further work and was cultured to yield that plasmid. The desired orientation of the ClaI fragment from pBSAGI5I in pA0802 had the AOX1 gene in the AOX1 locus oriented correctly to lead to the correct integration into the P. pastoris genome at the AOX1 locus of linearized plasmid made by cutting at the BglII site at the terminus of the 800 bp fragment from downstream of the AOX1 gene in the AOX1 locus.

pA0802 was then treated to remove the HBsAg coding segment terminated with an EcoRI site and a StuI site. The plasmid was digested with StuI and a linker of sequence:

5'-GGAATTCC-3'

3'-CCTTAAGG-5' was ligated to the blunt ends using T4 ligase. The mixture was then treated with EcoRI and again subjected to ligating using T4 ligase. The ligation mixture was then used to transform E. coli MC1061 to ampicillin resistance and transformants were screened for a plasmid of the expected size (5.1 kbp) with EcoRI-BglII fragments of about 1.78 kbp, 900 bp, and 2.42 kbp and BglII-ClaI fragment of about 100 bp, 2.32 kbp, 1.48 kbp, and 1.2 kbp. This plasmid was designated pA0803. A transformant with the desired plasmid was selected for further work and was cultured to yield pA0803.

Plasmid pA0804 was then made from pA0803 by inserting, into the BamHI site from pBR322 in pA0803, an approximately 2.75 kbp BglII fragment from the P. pastoris HIS4 gene. See, e.g., Cregg et al., Mol. Cell. Biol. 5, 3376 (1985) and European Patent Application Publication Nos 180,899 and 188,677. pA0803 was digested with BamHI and combined with the HIS4 gene-containing BglII site-terminated fragment and the mixture subjected to ligation using T4 ligase. The ligation mixture was used to transform E. coli MC1061 to ampicillin-resistance and transformants were screened for a plasmid of the expected size (7.85 kbp), which is cut by SalI. One such transformant was selected for further work, and the plasmid it harbors was designated pA0804.

pA0804 has one SalI-ClaI fragment of about 1.5 kbp and another of abut 5.0 kbp and a ClaI-ClaI fragment of 1.3 kbp; this indicates that the direction of transcription of the HIS4 gene in the plasmid is the same as the direction of transcription of the ampicillin resistance gene and opposite the direction of transcription from the AOX1 promoter.

The orientation of the HIS4 gene in pA0804 is not critical to the function of the plasmid or of its derivatives with cDNA coding segments inserted at the EcoRI site between the AOX1 promoter and terminator segments. Thus, a plasmid with the HIS4 gene in the orientation opposite that of the HIS4 gene in pA0804 would also be effective for use in accordance with the present invention.

The invention has been described in detail with reference to particular embodiments thereof. It will be understood, however, that variations and modifications can be effected within the spirit and scope of the invention.

That which is claimed is:

1. A DNA fragment, comprising one or more copies of an expression cassette that includes, in the direction of transcription, the following sequences of nucleotides:
    (i) a promoter region of a methanol responsive gene of a methylotrophic yeast,
    (ii) a sequence of nucleotides encoding a polypeptide consisting essentially of:
        (a) the S. cerevisiae AMF pre-pro sequence, including the processing site; Lys-arg-(glu-ala)$_x$, wherein x is an integer falling in the range of 0–3, inclusive, and
        (b) an aprotinin (APR) peptide; and
    (iii) a transcriptional terminator derived from a methanol responsive gene of a methylotrophic yeast,
wherein:
    the sequence of nucleotides encoding the AMF pre-pro sequence and the APR peptide are operationally associated, such that, upon transcription and translation of the transcript, biologically active APR peptide is secreted;
    the promoter and terminator are operationally associated with the DNA encoding the polypeptide, whereby the DNA including the polypeptide is transcribed; and said methanol responsive gene of a methylotrophic yeast is the *Pichia pastoris* AOX1 gene.

2. The DNA fragment of claim 1, wherein the APR peptide has a lysine in place of the N-terminal arginine of authentic APR.

3. The DNA fragment of claim 1, further comprising 3'- and 5'-ends having sufficient homology with a target gene of a yeast host for said DNA fragment to effect site directed integration of said fragment into said target gene, wherein the yeast host is a strain of *Pichia pastoris*.

4. The DNA fragment of claim 3 that is produced by SacI digestion of the *Pichia* expression vector selected from the group consisting of pAPR205, pAPR105, pAPR894, pAPR895, pAPR896 and pAPR897.

5. The DNA fragment of claim 3 that is produced by StuI digestion of the *Pichia* expression vector pAPR501.

6. A *P. pastoris* cell transformed with the DNA fragment of claim 3.

7. The cell of claim 6, wherein said cell is selected from the group consisting of cells of strains G+APR105S19, G+APR105S21, G+APR205S10, G+APR205S5, G+APR501S03, G+APR894-12, G+APR895-14, G+APR896-37 and G+APR897-28.

8. A culture of viable *P. pastoris* cells, comprising *P. pastoris*, cells, each of said *P. pastoris* cells having been transformed with the DNA fragment of claim 3.

9. A culture of viable *P. pastoris* cells, comprising *P. pastoris*, cells, each of said *P. pastoris* cells having been transformed with the DNA fragment of claim 3, wherein all of said *P. pastoris* cells are selected from the group consisting of cells of strains G+APR105S19, G+APR105S21, G+APR205S10, G+APR205S5, G+APR501S03, G+APR894-12, G+APR895-14, G+APR896-37 and G+APR897-28.

* * * * *